United States Patent
Flynn

(10) Patent No.: US 10,194,825 B2
(45) Date of Patent: Feb. 5, 2019

(54) METHODS AND APPARATUSES FOR THE LOCALIZATION AND TREATMENT OF DISEASE SUCH AS CANCER

(71) Applicant: Edward R Flynn, Albuquerque, NM (US)

(72) Inventor: Edward R Flynn, Albuquerque, NM (US)

(73) Assignee: Imagion Biosystems Inc., San Diego, CA (US)

( * ) Notice: Subject to any disclaimer, the term of this patent is extended or adjusted under 35 U.S.C. 154(b) by 322 days.

(21) Appl. No.: 14/973,542

(22) Filed: Dec. 17, 2015

(65) Prior Publication Data

US 2016/0136308 A1    May 19, 2016

Related U.S. Application Data

(63) Continuation-in-part of application No. 14/702,977, filed on May 4, 2015, and a continuation-in-part of
(Continued)

(51) Int. Cl.
*A61B 5/05* (2006.01)
*C07K 16/40* (2006.01)
(Continued)

(52) U.S. Cl.
CPC ........ *A61B 5/0515* (2013.01); *A61B 5/04005* (2013.01); *A61B 5/06* (2013.01);
(Continued)

(58) Field of Classification Search
CPC ... A61B 5/04005; A61B 5/0515; A61B 5/416; A61B 5/06; A61B 5/415; A61B 5/418;
(Continued)

(56) References Cited

U.S. PATENT DOCUMENTS

| 3,741,198 A | 6/1973 | Burton |
| 4,018,886 A | 4/1977 | Glaever |

(Continued)

FOREIGN PATENT DOCUMENTS

| WO | WO2001/74374 | 10/2001 |
| WO | WO2005/059118 | 6/2005 |

(Continued)

OTHER PUBLICATIONS

Adolphi et al., Characterization of magnetite nanoparticles for SQUID-relaxometry and magnetic needle biopsy, Feb. 20, 2009, Journal of Magnetism and Magnetic Materials, vol. 321, Is. 10, p. 1459-1464.

(Continued)

*Primary Examiner* — Bo Joseph Peng
(74) *Attorney, Agent, or Firm* — V. Gerald Grafe

(57) ABSTRACT

Embodiments of the present invention provide methods of detecting disease, methods of treating disease using targeted hyperthermia, methods of treating disease using targeted chemical agents, methods of treating disease comprising accurate measurements of the efficacy of treatments. The effect of nanoparticles on magnetic fields can be used to determine the location of a disease, and a measure of the number of cells characteristic of the disease. This location and measure can be used to guide therapy, and provide information regarding the most effective therapy to be applied. The same nanoparticles can be used to facilitate hyperthermia treatments, and to allow targeted application of chemical therapeutic agents.

14 Claims, 24 Drawing Sheets

Related U.S. Application Data application No. 13/703,051, filed as application No. PCT/US2011/039349 on Jun. 7, 2011, said application No. 14/702,977 is a continuation-in-part of application No. 13/503,674, filed as application No. PCT/US2010/055729 on Nov. 5, 2010, now Pat. No. 9,095,270.

(60) Provisional application No. 61/259,011, filed on Nov. 6, 2009, provisional application No. 61/308,897, filed on Feb. 27, 2010, provisional application No. 61/310,700, filed on Mar. 4, 2010, provisional application No. 61/314,392, filed on Mar. 16, 2010, provisional application No. 61/331,816, filed on May 5, 2010, provisional application No. 61/352,782, filed on Jun. 8, 2010, provisional application No. 61/361,998, filed on Jul. 7, 2010.

(51) Int. Cl.

| | | |
|---|---|---|
| *C07K 16/28* | (2006.01) | |
| *C07K 16/30* | (2006.01) | |
| *C07K 16/18* | (2006.01) | |
| *A61K 41/00* | (2006.01) | |
| *A61B 5/04* | (2006.01) | |
| *A61B 5/06* | (2006.01) | |
| *A61B 5/00* | (2006.01) | |
| *A61K 49/18* | (2006.01) | |
| *A61B 90/00* | (2016.01) | |

(52) U.S. Cl.
 CPC ............. *A61B 5/415* (2013.01); *A61B 5/418* (2013.01); *A61K 41/0052* (2013.01); *A61K 49/1875* (2013.01); *C07K 16/18* (2013.01); *C07K 16/2803* (2013.01); *C07K 16/2863* (2013.01); *C07K 16/2878* (2013.01); *C07K 16/2896* (2013.01); *C07K 16/3015* (2013.01); *C07K 16/3053* (2013.01); *C07K 16/3061* (2013.01); *C07K 16/3069* (2013.01); *C07K 16/40* (2013.01); *A61B 5/416* (2013.01); *A61B 2090/3954* (2016.02); *A61B 2562/0285* (2013.01)

(58) Field of Classification Search
 CPC .... A61B 2562/0285; A61B 2090/3954; C07K 16/40; C07K 16/2863; C07K 16/3069; C07K 16/3015; C07K 16/18; C07K 16/3061; C07K 16/2896; C07K 16/2878; C07K 16/2803; C07K 16/3053; A61K 41/0052; A61K 49/1875
 See application file for complete search history.

(56) References Cited

U.S. PATENT DOCUMENTS

| | | |
|---|---|---|
| 4,161,943 A | 7/1979 | Nogier |
| 4,346,715 A | 8/1982 | Gammell |
| 4,442,404 A | 4/1984 | Bergmann |
| 4,508,119 A | 4/1985 | Tukamoto |
| 4,574,782 A | 3/1986 | Borrelli |
| 4,590,922 A | 5/1986 | Gordon |
| 4,675,286 A | 6/1987 | Calenoff |
| 4,735,796 A | 4/1988 | Gordon |
| 4,829,984 A | 5/1989 | Gordon |
| 4,950,221 A | 8/1990 | Gordon |
| 5,043,101 A | 8/1991 | Gordon |
| 5,067,952 A | 11/1991 | Gudov |
| 5,203,782 A | 4/1993 | Gudov |
| 5,231,000 A | 7/1993 | Majocha |
| 5,384,109 A | 1/1995 | Klaveness |
| 5,486,161 A | 1/1996 | Lax |
| 5,496,534 A | 3/1996 | Klaveness |
| 5,715,837 A | 2/1998 | Chen |
| 5,735,279 A | 4/1998 | Klaveness |
| 5,738,837 A | 4/1998 | Klaveness |
| 5,759,793 A | 6/1998 | Schwartz |
| 5,782,764 A | 7/1998 | Werne |
| 5,921,244 A | 7/1999 | Chen |
| 5,935,123 A | 8/1999 | Edwards |
| 5,944,023 A | 8/1999 | Johnson |
| 6,123,920 A | 9/2000 | Gunther |
| 6,203,487 B1 | 3/2001 | Consigny |
| 6,348,185 B1 | 2/2002 | Piwnica-Worms |
| 6,400,980 B1 | 6/2002 | Lemelson |
| 6,459,924 B1 | 10/2002 | Creighton |
| 6,470,220 B1 | 10/2002 | Kraus |
| 6,485,985 B1 | 11/2002 | Weitschies |
| 6,514,481 B1* | 2/2003 | Prasad ................... A61N 1/406 324/307 |
| 6,660,002 B1 | 12/2003 | Edwards |
| 6,673,104 B2 | 1/2004 | Barry |
| 6,739,342 B1 | 5/2004 | Fredriksson |
| 6,821,504 B2 | 11/2004 | Wisniewski |
| 6,958,062 B1 | 10/2005 | Gough |
| 6,960,196 B2 | 11/2005 | Prindle |
| 6,997,863 B2 | 2/2006 | Handy |
| 7,053,109 B2 | 5/2006 | Schostarez |
| 7,074,175 B2 | 7/2006 | Handy |
| 7,081,123 B2 | 7/2006 | Merboth |
| 7,459,145 B2 | 12/2008 | Bao |
| 7,662,362 B2 | 2/2010 | Kuppusamy |
| 7,745,001 B2 | 6/2010 | Rosenzweig |
| 7,906,345 B2 | 3/2011 | Wang |
| 8,118,754 B1 | 2/2012 | Flynn |
| 8,447,379 B2 | 5/2013 | Flynn |
| 8,999,650 B2 | 4/2015 | Flynn |
| 2002/0123079 A1 | 9/2002 | Chen |
| 2002/0177769 A1 | 11/2002 | Orbach |
| 2003/0028071 A1* | 2/2003 | Handy ................... A61N 1/406 600/12 |
| 2003/0032995 A1 | 2/2003 | Handy |
| 2004/0156784 A1 | 8/2004 | Haase |
| 2004/0253181 A1 | 12/2004 | Port |
| 2005/0090732 A1 | 4/2005 | Ivkov |
| 2005/0249817 A1 | 11/2005 | Haik |
| 2006/0093555 A1 | 5/2006 | Torres |
| 2006/0140871 A1 | 6/2006 | Sillerud |
| 2006/0142749 A1 | 6/2006 | Ivkov |
| 2007/0037297 A1 | 2/2007 | Yoshinaga |
| 2007/0112339 A9 | 5/2007 | Ivkov |
| 2007/0118215 A1 | 5/2007 | Moaddeb |
| 2007/0140974 A1 | 6/2007 | Torres |
| 2007/0148095 A1 | 6/2007 | Chen |
| 2007/0166232 A1 | 7/2007 | Cho |
| 2007/0197900 A1 | 8/2007 | Baudenbacher |
| 2007/0205767 A1 | 9/2007 | Xu |
| 2007/0282200 A1 | 12/2007 | Johnson |
| 2008/0093219 A1 | 4/2008 | Goldberg |
| 2008/0213377 A1* | 9/2008 | Bhatia .............. A61K 47/48238 424/489 |
| 2009/0074673 A1 | 3/2009 | Janjic |
| 2009/0156659 A1 | 6/2009 | Butters |
| 2009/0169478 A1 | 7/2009 | Leuschner |
| 2009/0243610 A1 | 10/2009 | Ichihara |
| 2009/0295390 A1 | 12/2009 | Hahn |
| 2010/0008862 A1 | 1/2010 | Fu |
| 2010/0021391 A1 | 1/2010 | Douglas |
| 2010/0047180 A1 | 2/2010 | Zeng |
| 2010/0066363 A1 | 3/2010 | Brazdeikis |
| 2010/0120679 A1 | 5/2010 | Xu |
| 2010/0188075 A1 | 7/2010 | Litvinov |
| 2010/0219824 A1 | 9/2010 | Sillerud |
| 2012/0035458 A1 | 2/2012 | Flynn |
| 2012/0149029 A1 | 6/2012 | Flynn |
| 2013/0289383 A1 | 10/2013 | Flynn |

(56) References Cited

U.S. PATENT DOCUMENTS

2014/0112872 A1 4/2014 Flynn
2014/0322137 A1 10/2014 Flynn

FOREIGN PATENT DOCUMENTS

| WO | WO2007/021621 | 2/2007 |
|---|---|---|
| WO | WO2008/133726 | 11/2008 |
| WO | PCT/US2010/051417 | 5/2011 |
| WO | PCT/US2010/055729 | 5/2011 |
| WO | PCT/US2011/28746 | 9/2011 |
| WO | PCT/US2011/036349 | 12/2011 |

OTHER PUBLICATIONS

Jaetao et al., Enhanced Leukemia Cell Detection Using a Novel Magnetic Needle and Nanoparticles, Nov. 1, 2009, Cancer Research, Bol. 69, Is. 21, p. 8310-8316.
Stéphane Mornet Sebastien Vasseur, Fabien Grasset and Etienne Duguet, "Magnetic nanoparticle design for medical diagnosis and therapy" Journal of Materials Chemistry, 2004, 14, 2161-2175. retrieved from URL: http://pubs.rsc.org/en/content/articlelanding/2004/jm/b402025a.
Y. R. Chemla H. L. Grossman, Y. Poon, McDermott, R. Stevens, M. D. Alper, and J. Clarke, "Ultrasensitive magnetic biosensor for homogeneous immunoassay" Proc Natl Acad Sci U S A. Dec. 19, 2000; 97(26): 14268-14272, retrieved from URL: http://www.ncbi.nlm.nih.gov/pmc/articles/PMC18907/.
Leslie Laconte, Nitin Nitin, Gang Bao, "Magnetic nanoparticle probes", Materials Today, vol. 8, Issue 5, Supplement 1, May 2005, pp. 32-38, ISSN 1369-7021, retrieved from URL: http://www.sciencedirect.com/science/article/B6X1J-4G2FPKY-W/2/1301571fec686ec339a119ab10a5e17d.
Nanotechnology tackles brain cancer, National Cancer Institute Alliance for Nanotechnology in Cancer, Dec. 2005, 1-4.
Cecchelli, Romeo et al. Modelling of the blood-brain barrier in drug discovery and development, Nature Publishing Group, vol. 6 Aug. 1007, 650-661.
Cengelli, Feride et al. Interaction of functionalized superparamagnetic iron oxide nanoparticles with brain structures. The Journal of Pharmacology and Experimental Therapeutics vol. 318, No. 1 2006, 108-116.
Flynn, E.R. et al. A biomagnetic system for in vivo cancer imaging. Institute of Physics Publishing, Physics in Medicine and Biology. Phys. Med. Bio. 50 2005, 1273-1293.
Flynn, E.R. et al. Use of a SQUID array to detect T-cells with magnetic nanoparticles in determing transplant rejection. Journal of Magnetism and Magnetic Materials. Www.sciencedirect.com Dec. 2006, 429-435.
Haller, Andreas et al. Low TcSQUID measurement system for magnetic relaxation immunoassays in unshielded environment. IEEE Transactions on Applied Superconductivity, vol. 11, No. 1, Mar. 2001, 1371-1374.
Huddleston, Dan E. et al. Technology Insight: imaging amyloid plaques in the living brain with positron emission tomography and MRI. Nature Publishing Group vol. 1 No. 2. Dec. 2005, 96-105.
Michaelis, K. et al. Covalent linkages of apolipoprotein E to albumin nanoparticles strongly enhances drug transport into the brain. The Journal of Pharmacology and Experimental Therapeutics. vol. 317, No. 3 2006. 1246-1253.
Reddy, G.R. et al. Vascular targeted nanoparticles for imaging and treatment of brain tumors. American Association of Cancer Research. Www.aacrjournals.org. Nov. 15, 2006, 6677-6686.
Small, Gary W. et al. PET of brain amyloid and tau in mild cognitive impairment. The New England Journal of Medicine. Dec. 2006, 2652-2663.
Bryant, Howard et al.; Magnetic Needles and Superparamagnetic Cells. Phys. Med. Biol. 52 (2007) 4009-4025.
Bryant, Howard C., et al. Magnetic Properties of Nanoparticles Useful for SQUID Relaxometry in Biomedical Applications. (2010), doi:10:1016/j.jmmm.2010.10.042.
Hathaway, Helen, et al. Detection of Breast Cancer Cells Using Targeted Magnetic Nanoparticles and Ultra-Sensitive Magnetic Field Sensors. Breast Cancer Research 2011, 13:R108.
Johnson, Cort, et al. Magnetic Relaxometry with an Atomic Magnetometer and SQUID Sensors on Targeted Cancer Cells. Journal of Magnetism and Magnetic Materials 324 (2012) 2613-2619.
Adolphi, Natalie, et al. Imaging of Her2-targeted Magnetic Nanoaprticles for Breast Cancer Detection: Comaprions of Squid-detected Magnetic Relaxometry and MRI. Contrast Media and Molecular Imaging (2012). Doi: 10.10002/cmmi.499.
Butler, Kimberly, et al. Modeling the Efficiency of a Magnetic Needle for Collecting Magnetic Cells. Phys. Med. Biol. 59 (2014) 3319-3335.

* cited by examiner

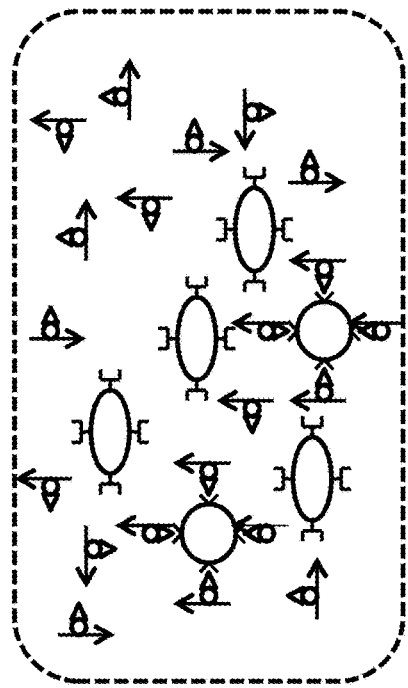
Fig. 2A
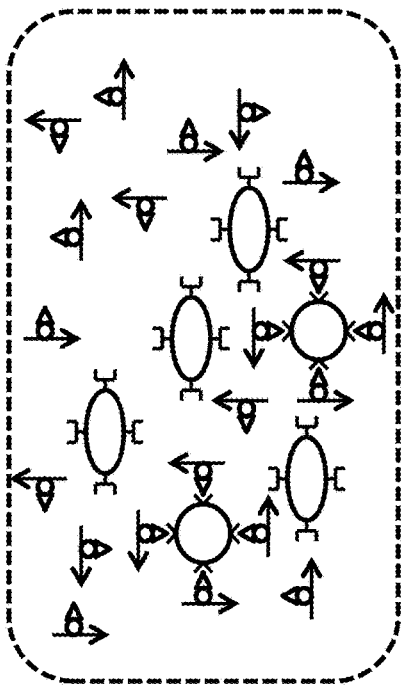
Fig. 2B
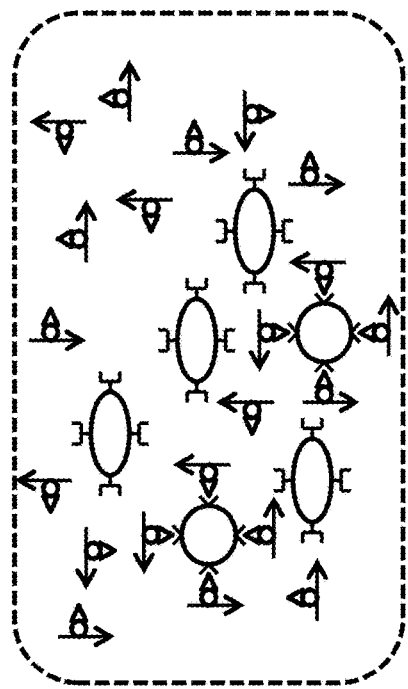
Fig. 2C
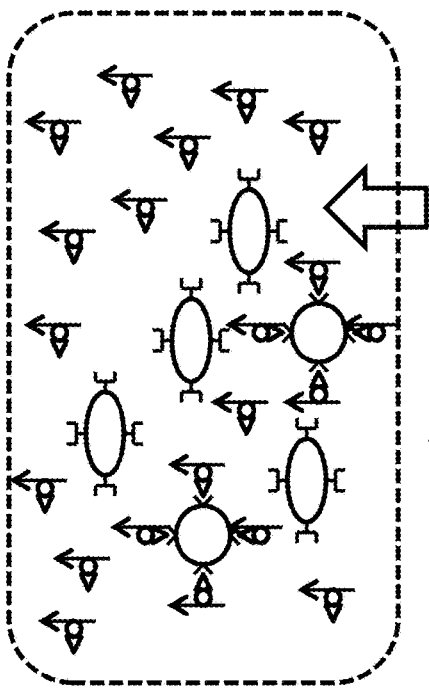
Fig. 2D
Fig. 2

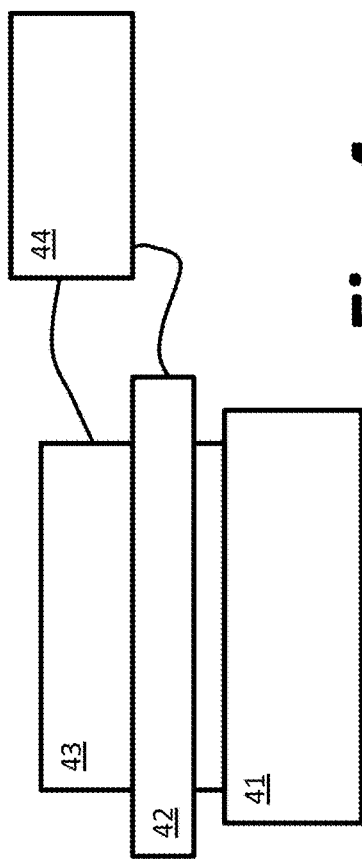
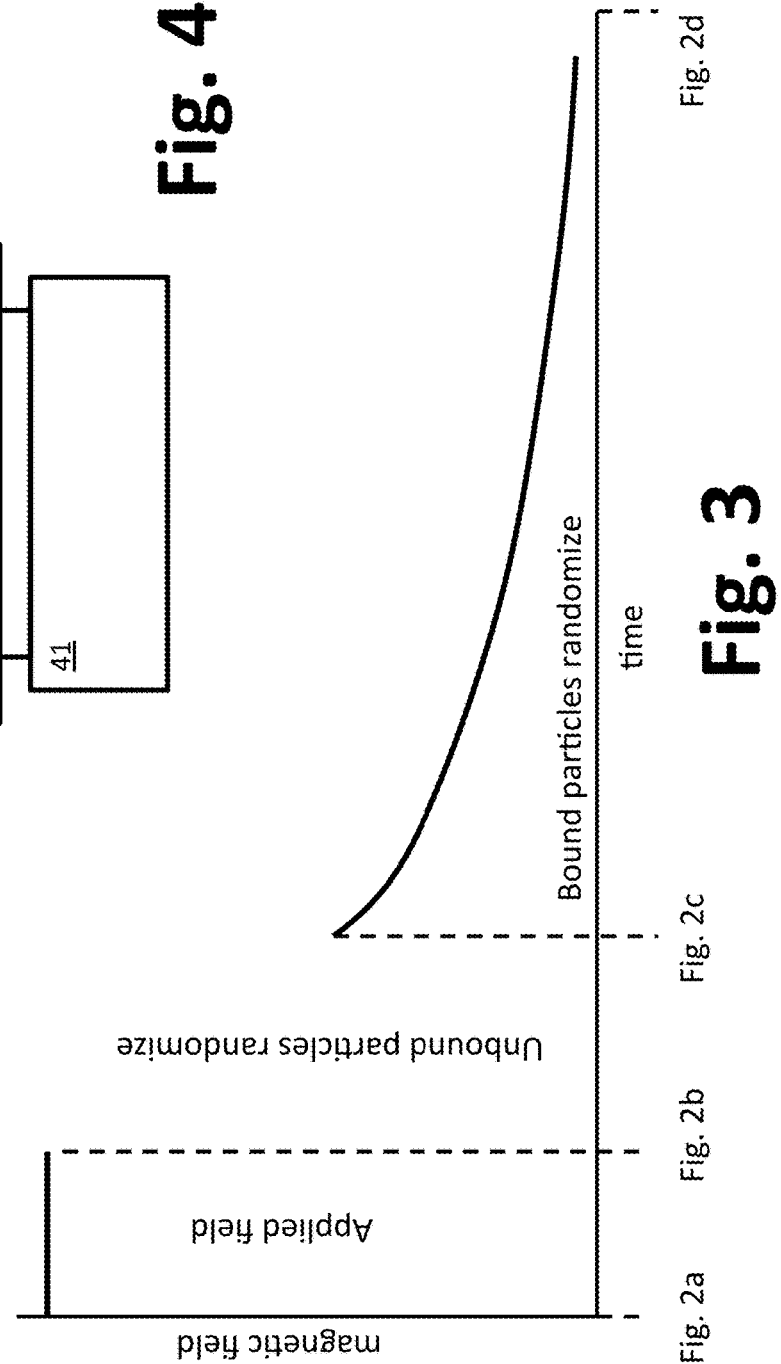

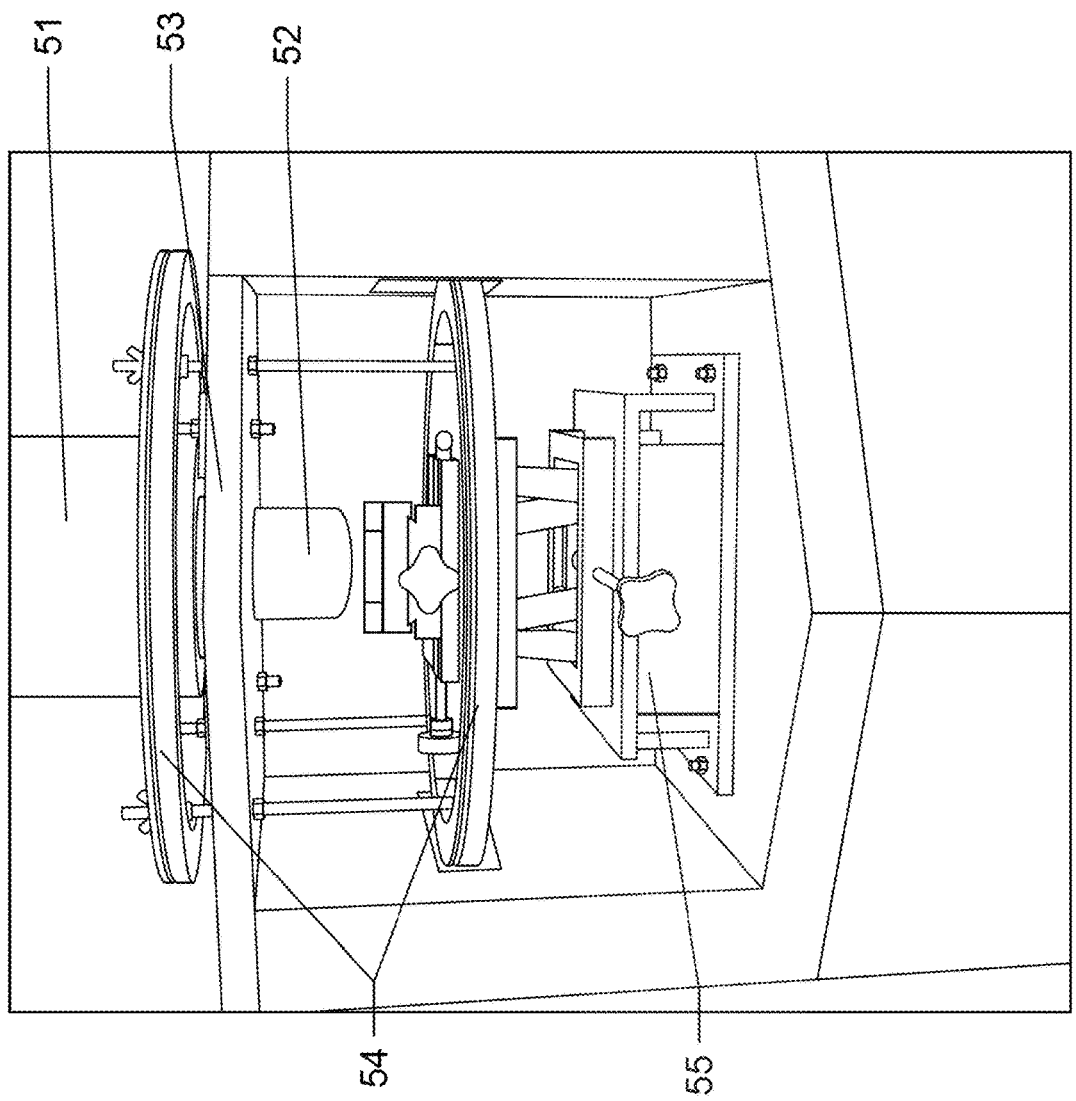

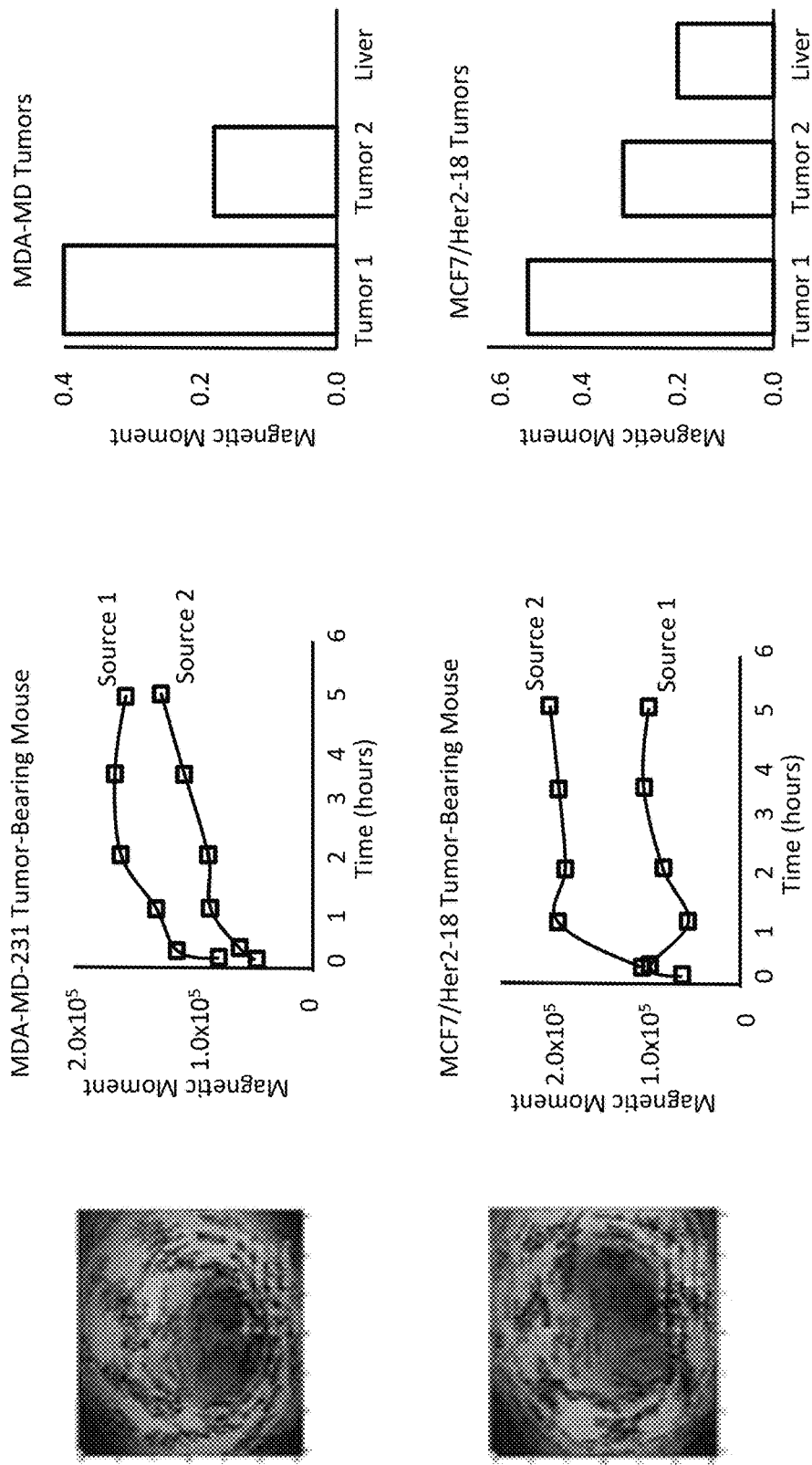

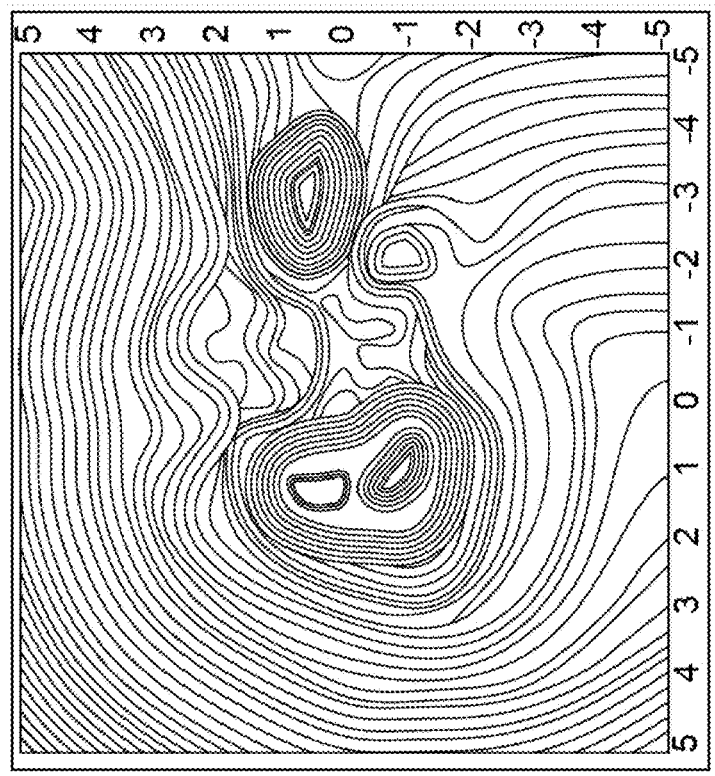
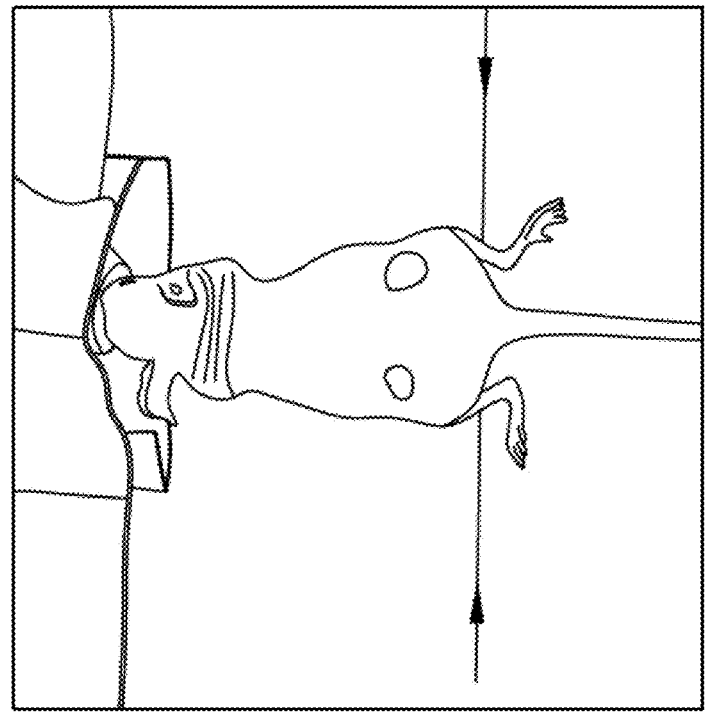
Fig. 25

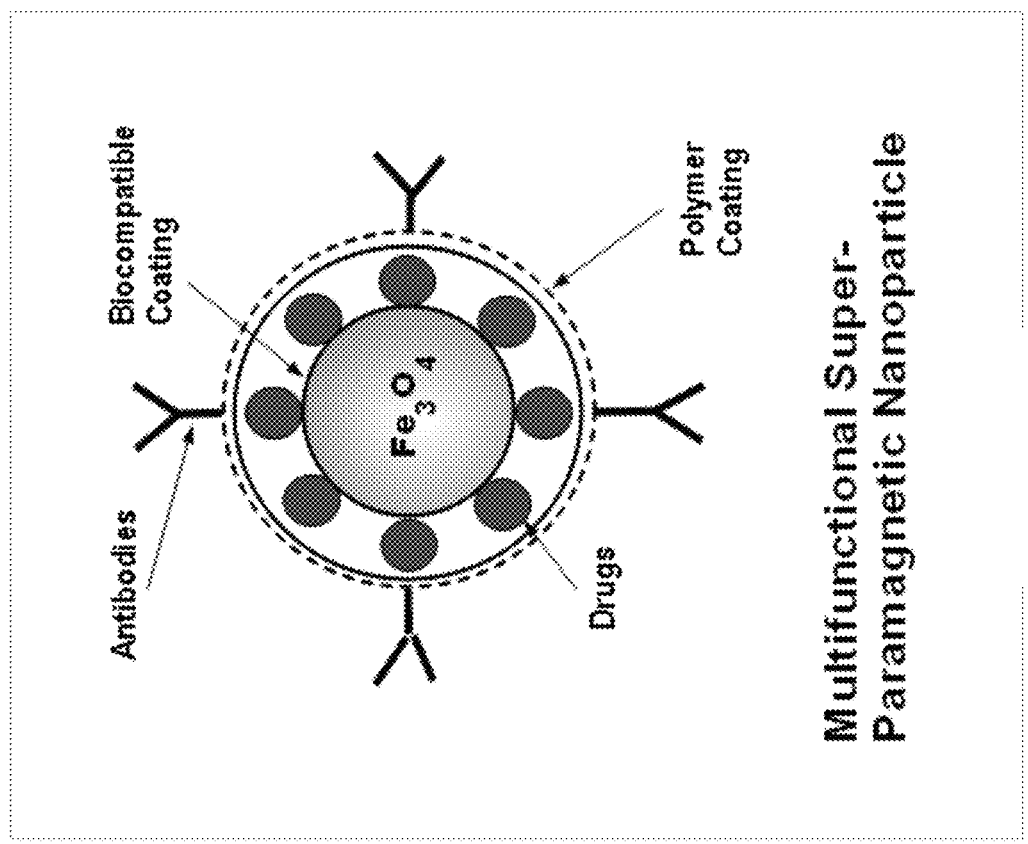

METHODS AND APPARATUSES FOR THE LOCALIZATION AND TREATMENT OF DISEASE SUCH AS CANCER

CROSS-REFERENCE TO RELATED APPLICATIONS

This application is a continuation in part of U.S. application Ser. No. 14/702,977, filed May 4, 2015, which application is a continuation of U.S. application Ser. No. 13/503,674, which was filed 16 May 2012 as a national stage application under 35 U.S.C. 371 of PCT application PCT/US2010/055729, filed 5 Nov. 2010, which claims priority to U.S. provisional applications 61/259,011 filed 6 Nov. 2009, 61/308,897 filed 27 Feb. 2010, 61/310,700 filed 4 Mar. 2010, 61/314,392 filed 16 Mar. 2010, 61/331,816 filed 5 May 2010, and 61/361,998 filed 7 Jul. 2010. This application is a continuation in part of U.S. application Ser. No. 13/703,051, which was filed Dec. 10, 2012 as a national stage application under 35 U.S.C. 371 of PCT application PCT/US11/39349, filed Jun. 7, 2011; which claims priority to U.S. provisional application 61/352,782. This application claims priority to each of the foregoing. Each of the foregoing is incorporated by reference herein.

TECHNICAL FIELD

This invention relates to cancer localization, treatment, monitoring of treatment and, in particular, the use of delivering hyperthermia, anti-cancer drugs, or a combination thereof, with targeted nanoparticles.

BACKGROUND ART

Early detection of disease allows the maximum likelihood of successful treatment and recovery. Furthermore, early detection and localization of the disease permits directed therapy to the site of the disease optimizing the efficiency of the treatment. With an appropriate detection device, the treatment can be monitored, further increasing the efficacy of the applied drugs or other forms of therapy. The ability to target specific diseases can also improve treatment outcomes. Early detection and localization of cancer, the second leading cause of death in the US, can improve patient outcomes. The most common methods used for clinical purposes for detection of cancer are all non-specific, i.e., they cannot distinguish between cancerous or benign tumors and none lead to 100% accurate detection. The available methods all have disadvantages and weaknesses, resulting in high rates of false diagnosis and too low a rate of positive diagnosis, together leading to increased mortality rates. The most common clinical modalities presently available are: (1) X-ray mammography, (2) magnetic resonance imaging (MRI), and (3) ultrasound scanning with (4) positron-emission tomography (PET) an additional option when available.

The measurement of X-ray attenuation provides information on the density of the intervening medium and is FDA approved and the most common device used to detect various forms of disease and, in particular, cancer. It is also responsible for many false-negative and false-positive results. Early stage cancer tumors can be detected but without specificity with regard to benign or cancerous tumors. Artifacts can be caused by healthy tissue and give rise to false positive results. Although the dose is low, there is increasing concern about the exposure to X-rays and radiation in general. Overall, the number of false positives in x-ray imaging of cancer remains high and the x-ray method cannot detect early-stage tumors.

Ultrasound is used to provide a second method for imaging tumors. Ultrasound has excellent contrast resolution but suffers from diminished spatial resolution compared to x-rays and other imaging techniques. Ultrasound is not currently approved by the FDA as a primary screening tool for cancer but is normally used as a follow up to investigate any abnormalities detected during routine. It is a tool often used to confirm suspect areas in x-ray images of breast and ovarian cancer.

MRI is used to follow up on potential problem areas seen during x-ray scans; however, the expense of a MRI scan often prohibits its use. MRI can detect small abnormalities in tissue and is also useful in determining if cancer has metastasized. Dynamic Contrast Enhanced (DCE) MRI potentially distinguishes between benign and cancerous tumors but produces a number of false positives. The expense of MRI limits its application as a screening tool. MRI imaging of cancer often uses magnetic nanoparticles as contrast agents and is an accepted protocol providing standards for the injection of such nanoparticles. Intravascular MRI contrast agents at a dose of about 2-5 mg/kg of nanoparticle weight have been used to detect metastatic lesions.

Because of the importance of early detection of disease, there are a variety of other techniques currently being studied for imaging. These include scintimammography using PET or SPECT, Impedance Tomography, and various forms of RF imaging.

Cancer is currently the second highest cause of death in the United States, second only to heart conditions. In 2009, approximately 570,000 people died of this disease, dominated by lung cancer (26-30%), breast cancer in women (15%) and prostate cancer in men (9%). Breast cancer results in 44,000 deaths a year in the United States; prostate cancer results in over 27,000 deaths. Early detection of cancer is important since discovery of tumors early minimizes the chances for metastatic transfers of the cancer to other parts of the body. Current methods for detecting cancer rely largely on (1) x-ray imaging (such as mammography in women's breast cancer), (2) ultrasound, (3) notice of physical changes, (4) MRI, and (5) PET scans. Routine screening is normally only done in mammography for women and for the genetically susceptible population. A large proportion of cancers are silent killers in that they express their presence only after metastasis and manifestation of severe discomfort. Early detection and treatment is difficult because of this and new approaches are extremely desirable.

Treatment of cancer once it is found can include any of a spectrum of methods, including surgery, chemotherapy, and ablation. Surgical removal of cancer is very effective if the cancer is contained in the primary site and is operable, but depends upon localization of the tumor. Normally, considerably more tissue is removed than the tumor itself in order to assure that all of the cancer is taken. Chemotherapy is the application of anti-cancer drugs and is normally done using injections of drugs that destroy cancer cells at a higher rate than normal cells. Typically chemotherapy is used to destroy fast growing cells and has therefore side effects affecting the digestive system and hair loss. Side effects can be severe with normal chemotherapy since the entire blood system is flooded with the chemicals. This can be particularly severe in young children with rapidly developing brains. Since traditional chemotherapy is non-localized and affects all of the body's organs it has a significant death rate associated with it. Ablation of tumors normally involves low temperature application (cryotherapy), or high temperature application (hyperthermia), to destroy cancer cells. Hyperthermia, as applied to cancer treatment, uses various devices to raise body tissue to sufficiently high temperatures, for example about 113° F. At these temperatures, cancer cells are damaged or killed. However, this must be done with minimal injury to normal tissues. The goal of cryotherapy and hyperthermia treatment is to shrink or eliminate cancerous tumors in the body. The location of the tumor must be ascertained beforehand. Typically, hyperthermia is applied over a much larger area than the known position of the tumor to make sure that the tumor is destroyed. X-rays or other imaging methods are then used to see if the tumor has been destroyed. These techniques have limitations based on sensitivity to tumor size and image contrast.

Hyperthermia is not well established as a clinical tool because studies have shown that the destruction of normal cells is excessive or there is insufficient destruction of localized tumors. A variety of methods for hyperthermia are used today including direct application of heat either localized or whole body through thermal blankets, the use of radio-frequency waves to heat up tissue, the use of optical techniques to use light (in particular infrared light), and heat probes inserted into tumors.

In general, hyperthermia is not normally used as the only therapy option when treating cancer but is combined with other forms of treatment, including radiation therapy, chemotherapy and anti-cancer drugs. Hyperthermia increases cancer cell sensitivity to other modalities, so the combination makes the other modalities more effective. When hyperthermia and radiation therapy are combined, they are often given within an hour of each other. Hyperthermia can also enhance the effects of certain anticancer drugs. The major organs exposed to hyperthermia include the breast, lungs, liver, cervix, and colon. Unfortunately, there is insufficient evidence that the current use of hyperthermia adds to patient survival times.

Hyperthermia is primarily applied locally in order to minimize damage to normal cells and organs not containing cancer. In these cases, the heating is accomplished through application of electromagnetic waves, typically in the hundreds of kHz to MHz, or the use of focused ultrasound. For implementation of these methods, the tumor position and size are predetermined by some imaging methods and the energy for heating is applied either through external means or internal probes. In this approach, the energy is focused in such a way as to minimize damage to normal tissue surrounding the tumor although inevitably damage does occur. This method is similar to cryo-ablation of tumors and removal of tumor cells, or ablation, occurs during the heating. This method is sometimes referred to as endocavitary or interstitial. Heating of larger body areas, including whole body hyperthermia, is used for larger tumors or when cancer has spread through the body. In these cases the body temperature can be raised to 108° F. either by immersion in a thermal bath or by application of RF heating over larger areas as discussed above.

In order to avoid serious side effects, the temperature of the affected regions during hyperthermia must be carefully monitored, commonly done using small inserted thermometers which are placed using various imaging devices. This can be a very painful procedure requiring local anesthesia. Normal tissue must be kept below 111° F. Proper application of hyperthermia is related to the temperature achieved during the treatment, as well as the length of treatment and cell and tissue characteristics. Although the goal of hyperthermia is not to destroy normal tissues by keeping the tissue temperature under 111° F., differences in tissue characteristics may cause hot spots resulting in burns, blisters, discomfort, or pain. Accurate localization of where the hyperthermia is applied can reduce the destruction of normal cells and permit higher concentration of energy applied to the tumor cells.

The standard application of chemotherapy is the direct injection of drugs into the body to treat the cancer. In most applications, one or more drugs are used to treat a variety of cancers and only certain drugs are specific to distinct cancer types. The drugs can be aimed directly at cancer cells or can be aimed at the rapidly growing vascular structure associated with a tumor. Although cancer cells are most affected by these drugs, many other cell types in the body also are harmed. The side effects can be life changing. The brain can suffer severe effects, sometimes referred to as "Chemo Brain," that can cause confusion and disorientation for years or for life. The effects on young children can cause loss of IQ and life-long memory problems. There may be short or long term skin, hair and intestinal changes. Peripheral neuropathy can also be induced and the resulting peripheral nerve damage can be permanent. Localization of drug concentration and effectiveness would allow a major change in chemotherapy application permitting the use of more advanced and specific drugs while minimizing the side effects of the drug.

In standard methods of application of therapy including hyperthermia and drug delivery, it is necessary to monitor the effects of the therapy by imaging methods that were used to determine the original location of the tumor. This is a very limiting procedure since the tumor had to have substantial size, e.g., several mm in diameter, before it could be detected originally and the knowledge of complete destruction of the tumor is limited by this detection size. Thus the normal method for monitoring the effectiveness of the treatment is to look for reoccurrence of the tumor. This also means that the treatment by hyperthermia or chemotherapy attempts to exceed the need to remove the tumor in order to make sure the therapy has succeeded resulting in increased unnecessary side effects. An effective means of monitoring the therapy would represent a major advance in the field of cancer treatment.

DISCLOSURE OF INVENTION

This application is related to the following applications, each of which is incorporated herein by reference: U.S. 61/259,011 filed 6 Nov. 2009; 61/308,897 filed 27 Feb. 2010; 61/314,392 filed 16 Mar. 2010; 61/331,816 filed 5 May 2010; 61/361,998 filed 7 Jul. 2010; each of which is incorporated herein by reference.

The present invention provides apparatuses and methods to detect cells or substances such as cancer cells in tissue. The description herein will refer to cancer or cancer cells for ease of description; the invention is applicable to other diseases and tissue states as well. An example system comprises a magnetic system, including a magnetic field generator that imposes a known magnetic field on tissue of the subject, magnetizing targeted superparamagnetic nanoparticles bound to, or internalized by, the cells or substance of interest; and including a sensitive magnetic sensor that can detect the residual magnetic field as the magnetization of the nanoparticles decays. An example magnetic system comprises a magnetic pulser, adapted to apply a uniform magnetizing pulse field to a cancer tissue of a patient placed on a measurement stage; and a remnant magnetic field detector such as a superconducting quantum interference device sensor, adapted to detect and analyze the residual magnetic field produced by decay of the magnetization of the nanoparticles after abatement of the applied pulsed field. The magnetic pulser can comprise a pair of Helmholtz coils. The remnant magnetic field detector can comprise an array of gradiometers coupled to superconducting quantum interference devices. Another example magnetic system comprises an atomic magnetometer and an array of atomic gradiometers-very sensitive magnetic field sensors that can be used to measure extremely weak magnetic fields based on the Larmor precession of atoms in a magnetic field. In some embodiments of the present invention, the atomic magnetometer comprises a chip set containing a small cavity containing an atomic vapor cell. This vapor cell contains Rb atoms, and is optically pumped by circularly polarized laser beam. The atoms go through a Larmor precession and the frequency of this precession causes a change in the index of refraction of the vapor in response to an applied magnetic field. A second laser can be used as a measuring field for this change in refraction using a set of gratings to measure interference pattern changes as the applied magnetic field changes. Other atomic magnetometers can also be suitable, for example atomic magnetometers such as those described by Flynn et al. in "Magnetic relaxometry with an atomic magnetometer and SQUID sensors on targeted cancer cells," Journal of Magnetism and Magnetic Materials 324 (2012) 2613-2619, incorporated herein by reference. The vapor cells can be single or arranged in a gradiometer configuration to measure the changes in field as a function of distance.

A method according to the present invention comprises providing the magnetic system; injecting a plurality of targeted (e.g., labeled with an antibody) superparamagnetic nanoparticles into a subject for specific binding to the cancer cells or other cells or substance of interest; applying a known (e.g., uniform) magnetizing pulse field to magnetize the nanoparticles in the subject tissue; and detecting the residual magnetic field of the magnetized nanoparticles thereby providing an image of the nanoparticles bound to the cancer tissue of the patient. The targeted superparamagnetic nanoparticle can comprise a magnetic core coated with a biocompatible coating to which is attached at least one specific cell-surface antibody (or other binding agent) or substance that encourages endocytosis by the cells of interest. For example, the magnetic core can comprise a ferromagnetic material, such as iron oxide. Examples of suitable targeting agents such as antibodies are described below.

BRIEF DESCRIPTION OF DRAWINGS

The accompanying drawings, which are incorporated in and form part of the specification, illustrate the present invention and, together with the description, describe the invention. In the drawings, like elements are referred to by like numbers.

FIGS. 2A, 2B, 2C, 2D provide a schematic illustration of an example measurement in accord with the present invention.

FIG. 3 is a schematic illustration of measurements from the process described in connection with FIG. 2.

FIG. 4 is a schematic illustration of an apparatus suitable for use in the present invention.

FIG. 5 is a schematic illustration of an exemplary apparatus using superconducting quantum interference device (SQUID) magnetic sensors.

FIG. 15 is an illustration of the magnetic contour lines observed for 35 different measurement sites FIG. 16 is an illustration of the time course of the measurements for the two mice and both tumors of each mouse.

FIG. 17 is an illustration of the results of these measurements and show very good agreement with the in-vivo measurements on the live mouse.

FIG. 25 is a photograph of a mouse used to verify that the SQUID sensor method works in-vivo along with magnetic contour fields from the mouse.

FIG. 32 is an illustration of a multifunctional superparamagnetic nanoparticle containing anti-cancer drugs in a polymer coating.

MODES FOR CARRYING OUT THE INVENTION AND INDUSTRIAL APPLICABILITY

The present invention is described in the context of various example embodiments and applications. In some of the description, the term "detection" is used for brevity; the invention can provide for the detection of the presence of cells or substances, measurement of the number of cells or amount of substance, determination of the location of cells or substance, determination of the change or rate of change in the preceding, and similar determinations, all of which are included in the term "detecting." The description below is in the context of cell surface markers and antibodies to immobilize nanoparticles on the surface of cells; the invention can also employ coatings that encourage endocytosis and result in particles immobilized internal to cells.

Figure 1:
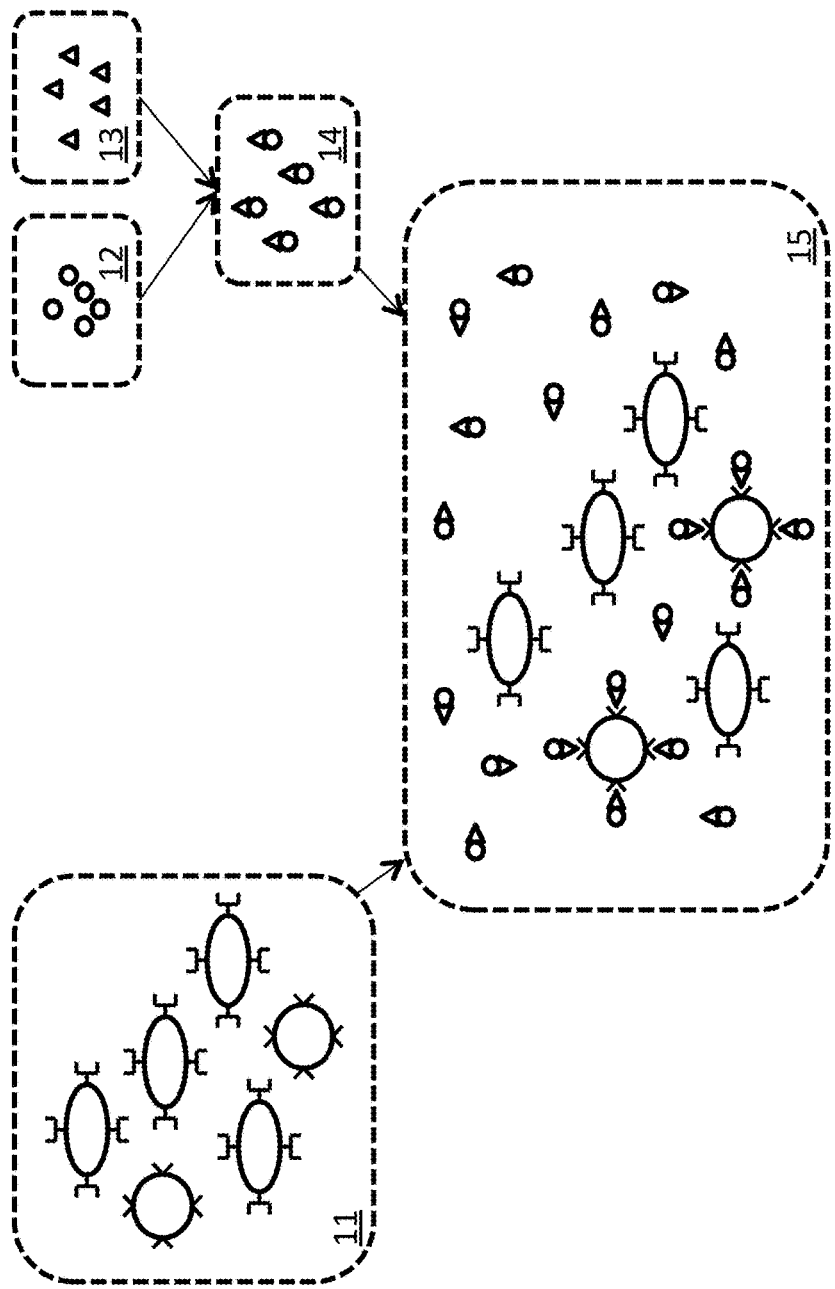
FIG. 1 is a schematic illustration of an example preparation of tissue of a subject for measurement according to the present invention.

A simplified example of magnetic relaxation measurement according to the present invention is first described. FIG. 1 is a schematic illustration of an example preparation of tissue of a subject for measurement according to the present invention. The illustrations in the figure are highly simplified and intended for ease of explanation only, and are not intended to represent the actual shapes, sizes, proportions, or complexities of the actual materials involved. A portion of the tissue 11, e.g., an organ to be investigated, or a known or suspected tumor site, comprises some cells of the type of interest (shown in the figure as circles with "V" shaped structures around the periphery) and some cells of other types (shown in the figure as ovals with rectangular structures around the periphery). A plurality of magnetic nanoparticles 12 is provided, shown in the figure as small circles. A plurality of targeting molecules 13 is also provided, shown in the figure as small triangles. The nanoparticles and targeting molecules are combined (or conjugated), forming targeted nanoparticles 14.

The targeted nanoparticles can then be introduced to the tissue 15. Cells of the type of interest have binding sites or other affinities for the targeting molecule, illustrated in the figure by "V" shaped structures around the periphery of such cells. The targeting molecules attach to the cells of the type of interest, illustrated in the figure by the triangular targeting molecules situated within the "V" shaped structures. Generally, each cell will have a large number of such binding or affinity sites. Cells of other types do not have such binding sites or affinities, illustrated in the figure by ovals with no targeted nanoparticles attached. Targeted nanoparticles that do not bind to cells are left free in the prepared sample, illustrated in the figure by small circles with attached triangles that are not connected with any specific cell.

FIGS. 2A, 2B, 2C, 2D provide a schematic illustration of an example measurement in accord with the present invention. In FIG. 2A, the tissue is as in FIG. 1, with the addition of arrows near each nanoparticle. The arrows are representative of the magnetization of each nanoparticle, and indicate that the magnetization of the nanoparticles in the tissue is random (in the figure, the arrows are shown in one of four directions for ease of illustration only; in practice the magnetization can have any direction).

In FIG. 2B, an external magnetic field (represented by the outlined arrow at the lower right of the figure) is applied. The magnetization of the nanoparticles in response to the applied magnetic field is now uniform, represented in the figure by all the magnetization arrows pointing in the same direction.

FIG. 2C illustrates the tissue a short time after the magnetic field is removed. The nanoparticles not bound to cells are free to move by Brownian motion, and their magnetization rapidly returns to random, represented in the figure by the magnetization arrows of the unbound nanoparticles pointing in various directions. The nanoparticles bound to cells, however, are inhibited from such physical motion and hence their magnetization remains substantially the same as when in the presence of the applied magnetic field.

FIG. 2D illustrates the prepared sample a longer time after removal of the applied magnetic field. The magnetization of the bound nanoparticles has by now also returned to random.

FIG. 3 is a schematic illustration of measurements from the process described in connection with FIG. 2. Magnetic field is shown as a function of time in a simplified presentation for ease of illustration; in actual practice the units, scales, and shapes of the signals can be different and more complex. At the beginning of the process, corresponding to the state of FIG. 2A, the nanoparticle magnetization is random and the external magnetic field is applied. After that time, the magnetization of the nanoparticles is uniform, corresponding to the state of FIG. 2B. The magnetic field can be ignored for a short time while the unbound nanoparticles return to random magnetization, corresponding to the state of FIG. 2C. The magnetization can then be measured as the bound nanoparticles transition from uniform to random magnetization, corresponding to the state of FIG. 2D. The characteristics of the measurement magnetization from the state of FIG. 2C to that of FIG. 2D are related to the number of bound nanoparticles in the sample, and hence to the number of cells of the type of interest in the sample.

FIG. 4 is a schematic illustration of an apparatus suitable for use in the present invention. A subject stage 41 is configured to dispose the subject in an effective relationship to the rest of the apparatus. A magnetizing system 42, for example Helmholtz coils, mounts relative to the subject stage so that the magnetizing system can apply a magnetic field to the sample. A magnetic sensor system 43 mounts relative to the subject stage so that it can sense the small magnetic fields associated with the magnetized nanoparticles. The system is controlled and the sensor data analyzed by a control and analysis system 44; for example by a computer with appropriate programming.

FIG. 5 is a schematic illustration of an exemplary apparatus using superconducting quantum interference device (SQUID) magnetic sensors. A liquid helium reservoir dewar 51 at the top of the picture maintains the temperature of the SQUID sensors. SQUID 2nd-order axial gradiometers are contained in a white snout 52 protruding through a support frame 53. There are seven gradiometers contained within this exemplary snout; one in the center and 6 in a circle of 2.15 cm radius. Each gradiometer is inductively coupled to a low temperature SQUID. Two circular coils 54 form a Helmholtz pair that can provide a magnetizing pulsed field for the nanoparticles. The uniform field produced by these coils can be varied but typically is 40 to 50 Gauss and the pulse length is typically 300-800 msec. In this example, a wooden frame supports the SQUID and the measurement platform as well as the magnetizing coils. The non-magnetic support system comprises a 3-dimensional stage 55 that can be constructed with no metal components, e.g., of plastic. The upper two black knobs control the x-y stage movements over a +/−10 cm range and the lower knob is used to raise and lower the measurement stage over a 20 cm range. A sample holder can be inserted onto the stage that can contain live subjects such as mice or other small animals.

Figure 6:
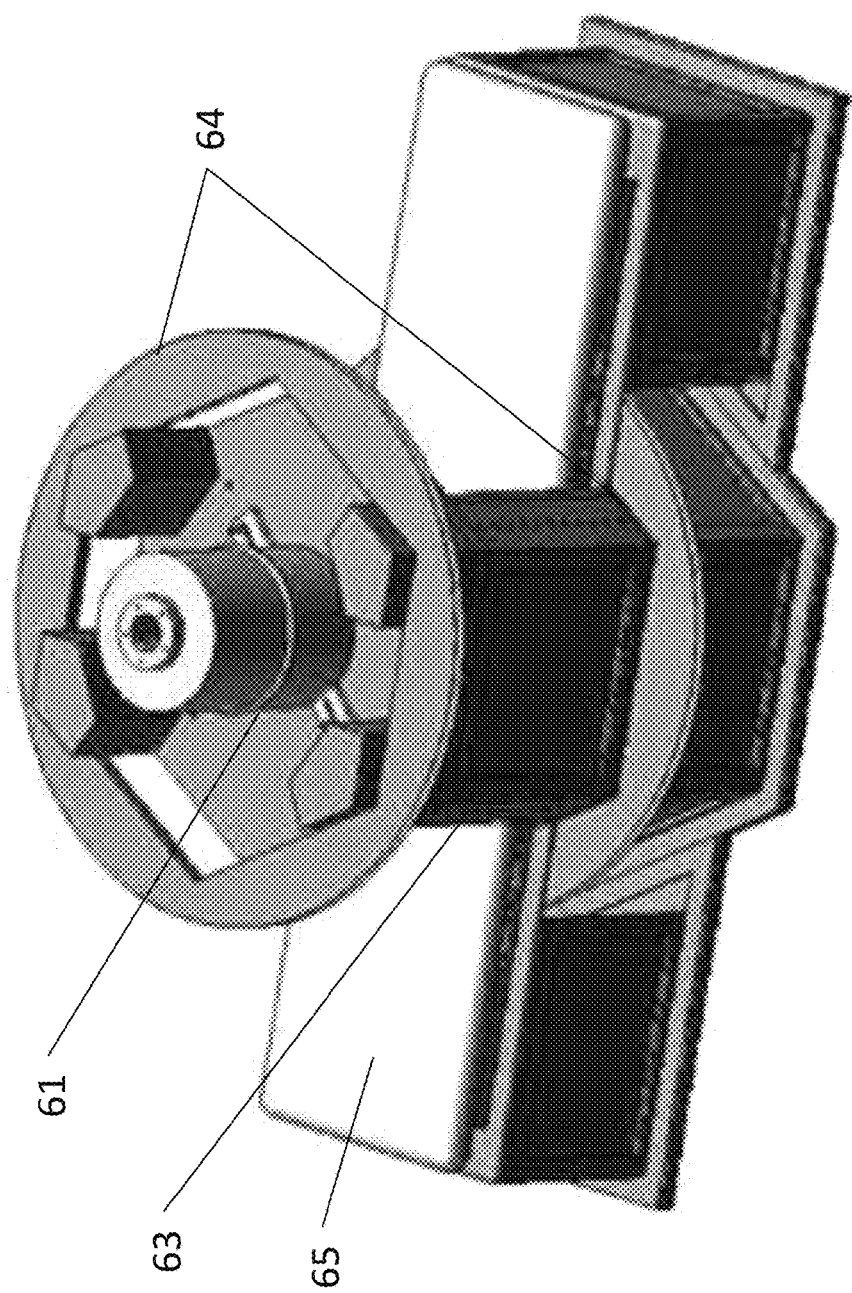
FIG. 6 is a schematic illustration of an exemplary SQUID sensor apparatus that can be used for human cancer examinations.

FIG. 6 is a schematic illustration of an exemplary SQUID sensor apparatus that can be used for human cancer examinations. A wooden structure 63 can be similar to the support frame shown in FIG. 5. The measurement stage can be replaced by a bed 65 for patient placement. Two larger Helmholtz coils 64 comprise the wooden circular forms above and below the bed. These larger coils can be used to generate a uniform pulse field and magnetize the magnetic nanoparticles that have been injected into the patient. The currents can be modified, e.g., increased, from those used in the apparatus shown in FIG. 5 to again produce fields in the range of 40 to 50 Gauss. Similar to the apparatus shown in FIG. 5, a SQUID dewar 61 with an array of magnetic gradiometers can be used to measure the residual magnetic field change produced by the magnetized nanoparticles.

Figure 7:
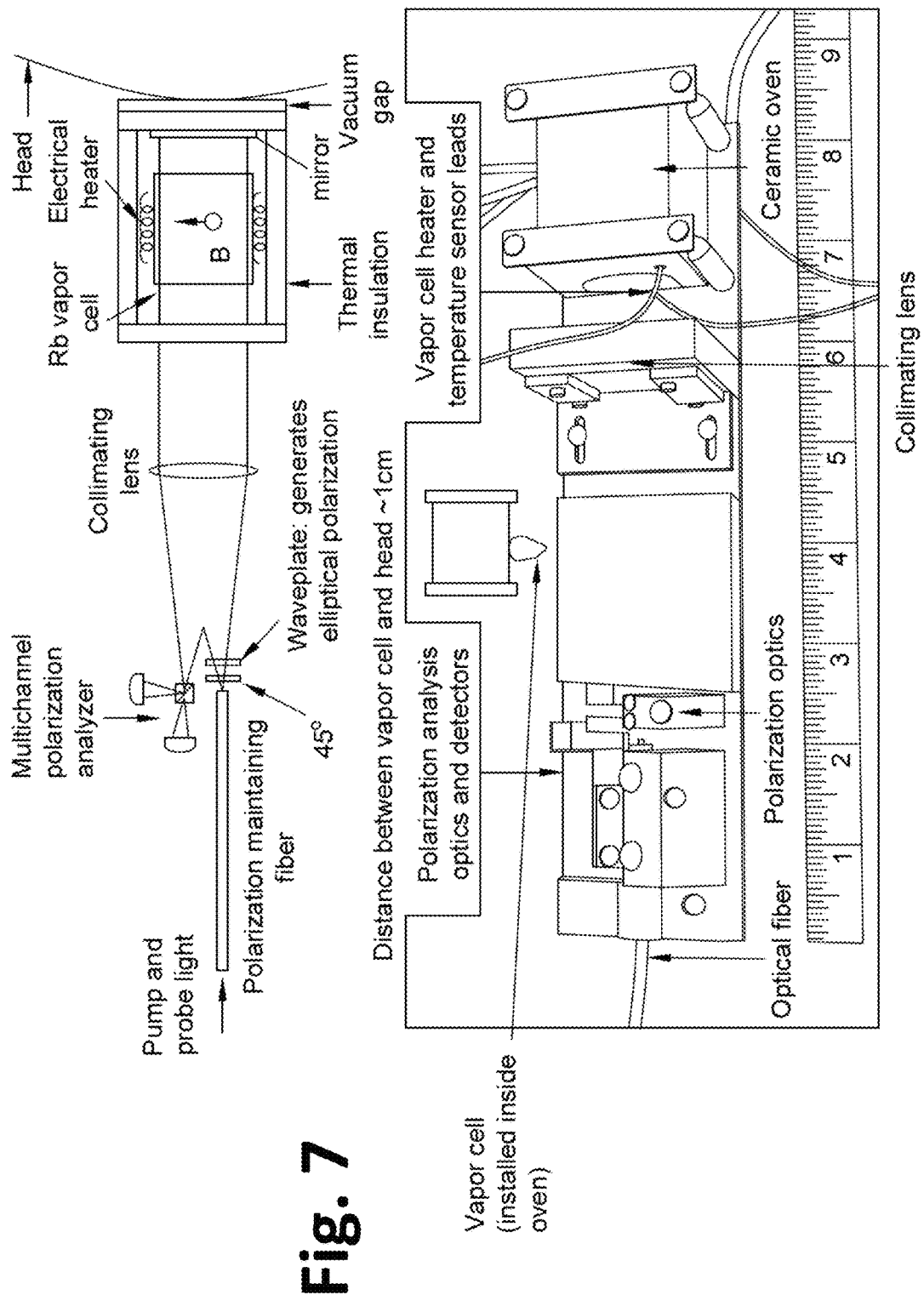
FIG. 7 is a schematic illustration and photo of an atomic magnetometer for weak field measurements.

FIG. 7 is a schematic and photo of an atomic magnetometer for weak field measurements. This device is miniaturized by using microchip fabrication methods and multiple units can be placed side-by-side to form an array of sensors. The operation of the magnetometer is through application of a laser light beam applied through an optical fiber. This beam pumps the heated Rb gas in the vapor cell into specific atomic states. The beam is first elliptically polarized and collimated into the vapor cell. A mirror reflects this beam back through the cell and lens into a polarization analyzer. A magnetic field applied perpendicular to the length of the magnetometer changes the direction of the polarized atoms or index of refractionof the gas in the cell, changing the polarization of the light through the cell. The change in polarization yields the magnitude of the applied magnetic field. The pumping laser supplies multiple fiber optic cables and is thus used for multiple magnetometers. An array of these magnetometers for relaxometry measurements can comprise 7 vapor cells placed with one in the center surrounded by 6 more. The applied field from the magnetizing coils is perpendicular to the arrangement shown in FIG. 5 in order to induce the maximum observable magnetic moments into the nanoparticles. The photo at the bottom of FIG. 7 shows an exemplary physical arrangement and size of the atomic magnetometer for application with the present invention. The sensitivity of the device shown is 0.16 fT/$\sqrt{Hz}$, compared to sensitivity of an exemplary SQUID system as shown in FIG. 5 of 1.0 pT/$\sqrt{Hz}$ (1000 fT/$\sqrt{Hz}$). Atomic magnetometers require no cryogenic coolant which can make them desirable for clinical applications where such coolants, in particular liquid helium, are not always readily obtainable.

Example Application to Detection of Breast Cancer.

For breast cancer, the current method of choice for screening and detection is mammography. While mammography has led to a significant improvement in our ability to detect breast cancer earlier, it still suffers from the inability to distinguish between benign and malignant lesions, difficulty in detecting tumors in dense and scarred breast tissue, and fails to detect 10-30% of breast cancers. The use of magnetic nanoparticles conjugated to tumor-specific reagents combined with detection of these particles through measurement of their relaxing fields represents a promising new technology that has the potential to improve our ability to detect tumors earlier. Furthermore, detection of targeted magnetic nanoparticles using weak field sensors is fast and is can be more sensitive than MRI detection because only particles bound to their target cells are detected.

We have developed conjugated magnetic nanoparticles targeted to breast cancer cells that express the HER2 antigen, which is overexpressed on ~30% of human breast cancers. We have characterized the nanoparticles for their magnetic properties and selected those of optimal size and magnetic moment per mg of Fe. A number of different cell lines that have specificity to HER2 have been studied to determine their site density and sensitivity of the sensor system for detection. A SCID mouse model was explored using tumors grown from human cell lines, imaging the mouse under the sensor system followed by confirming histology studies. These results indicate the validity of the magnetic sensor approach for sensitive detection of breast cancer.

Figure 8:
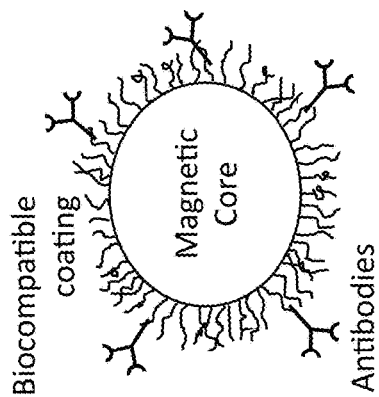
FIG. 8 is schematic illustration of a magnetic nanoparticle with biocompatible coating and attached antibodies for targeting specific cells.
Figure 9:
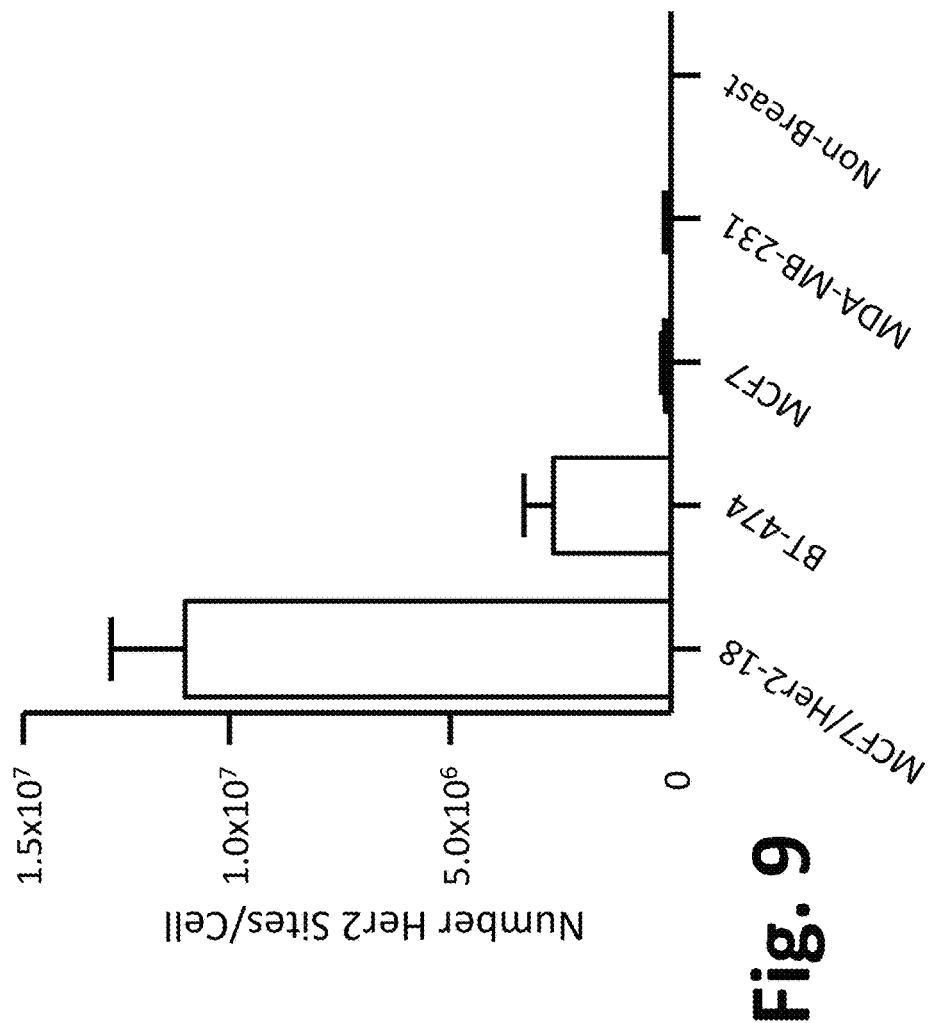
FIG. 9 is a depiction of the number of Her2 sites per cell calculated by comparison to a range of microspheres with known binding capacities.

FIG. 8 is schematic illustration of a magnetic nanoparticle with biocompatible coating and attached antibodies for targeting specific cells. In a demonstration of an example embodiment of the present invention, we used HER2 Antibodies (Ab) that are specific to 30-40% of breast cancers. The nanoparticles had coatings containing Carboxyl groups and a Sulfo-NHS method is used to conjugate the nanoparticles to the antibodies. Flow cytometry performed for breast cancer cell lines MCF7, MCF7/Her218 (MCF7 clone stably transfected with Her2), BT474, and MDA-MB-231. Number of Her2 binding sites determined by flow cytometry, Anti-Her2 antibodies conjugated to the fluorescent probe FITC. FIG. 9 is a depiction of the number of Her2 sites per cell calculated by comparison to a range of microspheres with known binding capacities. MCF7 cells engineered to overexpress Her218 have $11 \times 10^6$ Her2 binding sites/cell, BT-474 have $2.8 \times 10^6$, MCF7 $0.18 \times 10^6$, MDA-MB-231 $0.11 \times 10^6$. Non-breast cell lines have <4000 Her2 binding sites/cell.

Figure 10:
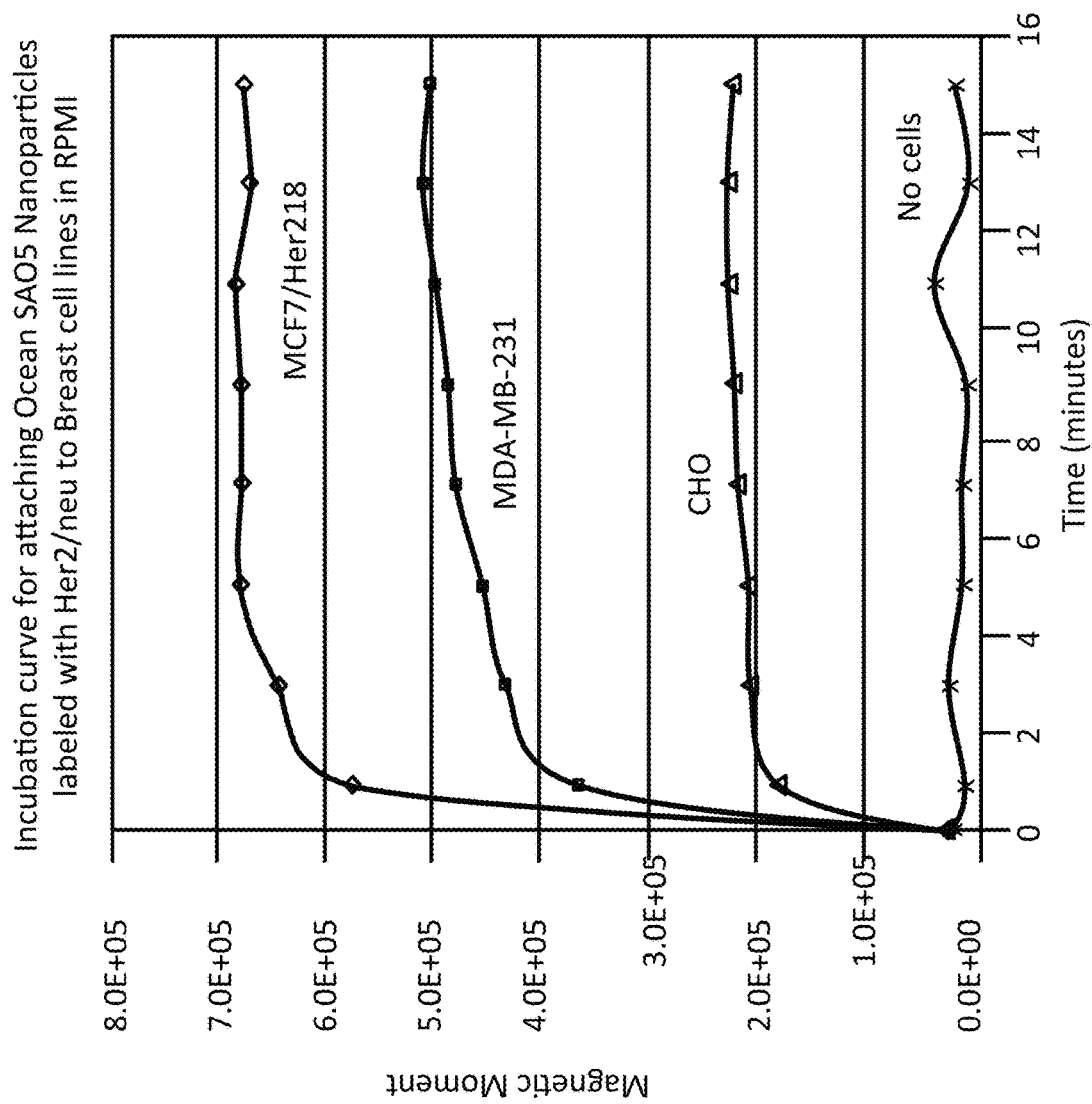
FIG. 10 is an illustration of magnetic moments of two breast cancer cell lines, MCF7/HER218 and MDA-MB-231 measured as function of time after incubating with HER2/neu antibodies and nanoparticles.

FIG. 10 is a graph of a measurement of the magnetic moment in the SQUID sensor system as a function of time for incubation of attaching magnetic nanoparticles (from Ocean Nanotech) to breast cancer cell lines. The magnetic nanoparticles were coated with a carboxyl biocompatible coating and were then conjugated to the Her2/neu antibody. This antibody is specific to approximately 30% of breast cancer cells in humans. The labeled magnetic nanoparticles were inserted into vials containing live cancer cells and the magnetic moments of the vial measured at various times ranging from one minute to 16 minutes. The zero time point is the magnetic moment of the vial of nanoparticles before adding to the cells. The lack of magnetic moment for the unmixed particles is a demonstration that unbound particles give no magnetic signal with this SQUID imaging method. Upon mixing with the cells, the magnetic moments increase rapidly and saturate indicating that the cells have collected on their surfaces the maximum number of nanoparticles possible in one to two minutes. The top curve is for the breast cancer cell line, MCF7/Her218 that is known to be very specific for the Her2/neu antibody and the large magnitude of the magnetic signal verifies this. The breast cancer cell line, MDA-MB-231, is also positive for Her2/neu but with much fewer sites for the antibody targeted nanoparticles to attach to. The smaller magnitudes are also indicative of this trend. The CHO cell line is non-specific to Her2/neu and gives substantially smaller magnetic moments after incubation. The presence of a magnetic moment is indicative of some phagocytosis of these cells where the nanoparticles enter the cells. The curve for no cells is for the vials containing nanoparticles only and shows that the particles alone continue to give no signal and thus there is no agglomeration occurring of the particles. These results demonstrate the specificity of the antibody for the target cancer cells and verify that only bound particles give magnetic moments. This result is not true for other methods such as MRI which sees all particles, bound or unbound.

Figure 11:
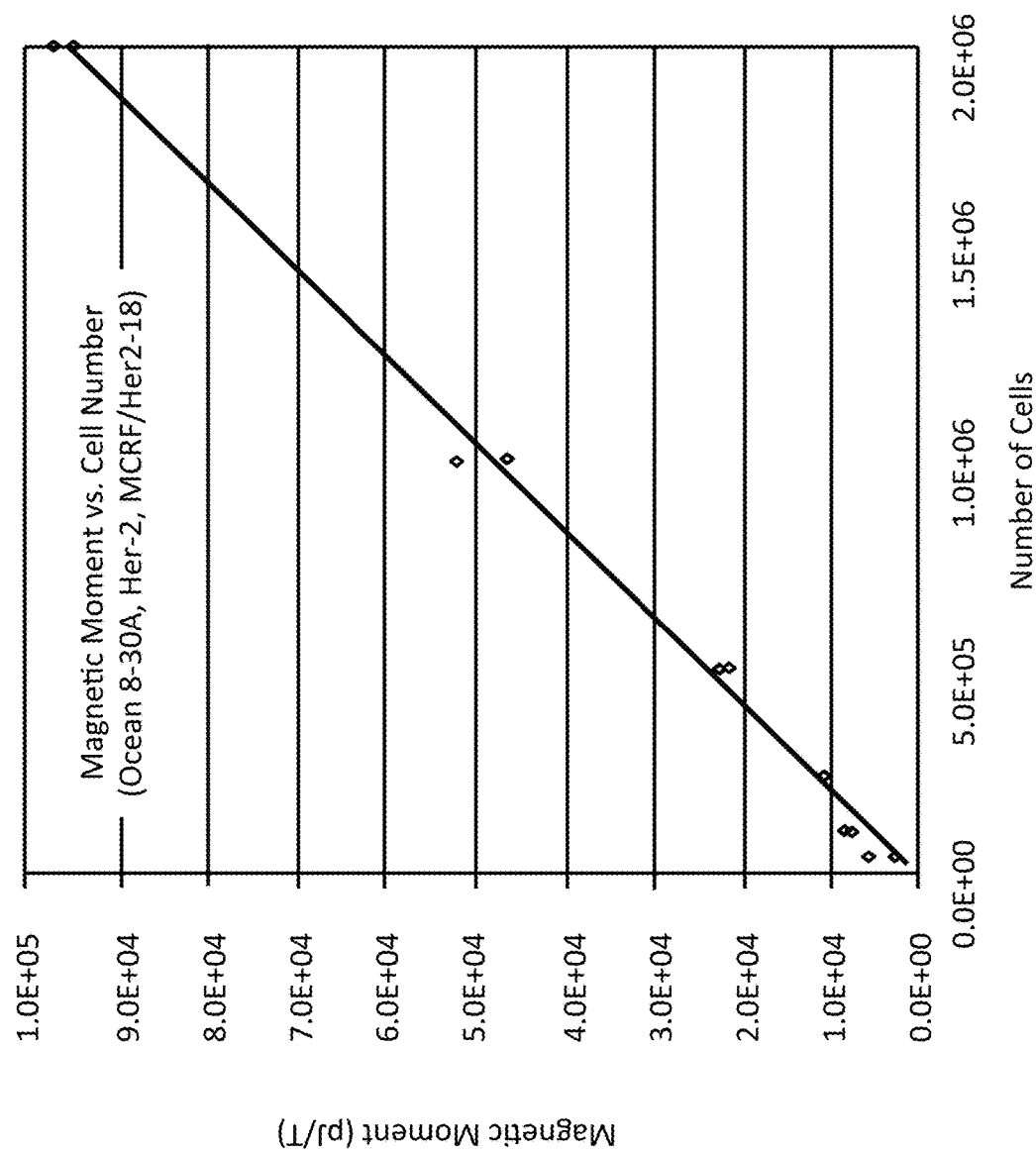
FIG. 11 is an illustration of the magnetic moments of cell samples measured as function of number of cells by pipetting cells down by factors of two.

FIG. 11 is an illustration of the magnetic moments of cell samples measured as function of number of cells by pipetting cells down by factors of two. The demonstrated sensitivity is 100,000 cells forMCF7 cells and Ocean nanoparticles, for cells 3.5 cm from the sensor. There are $2.5 \times 10^6$ np/cell. Linearity demonstrates magnetic moment yields # of cells; MRI contrast is not a linear function of cell number. A typical mammogram requires 10 million cells.

Figure 12:
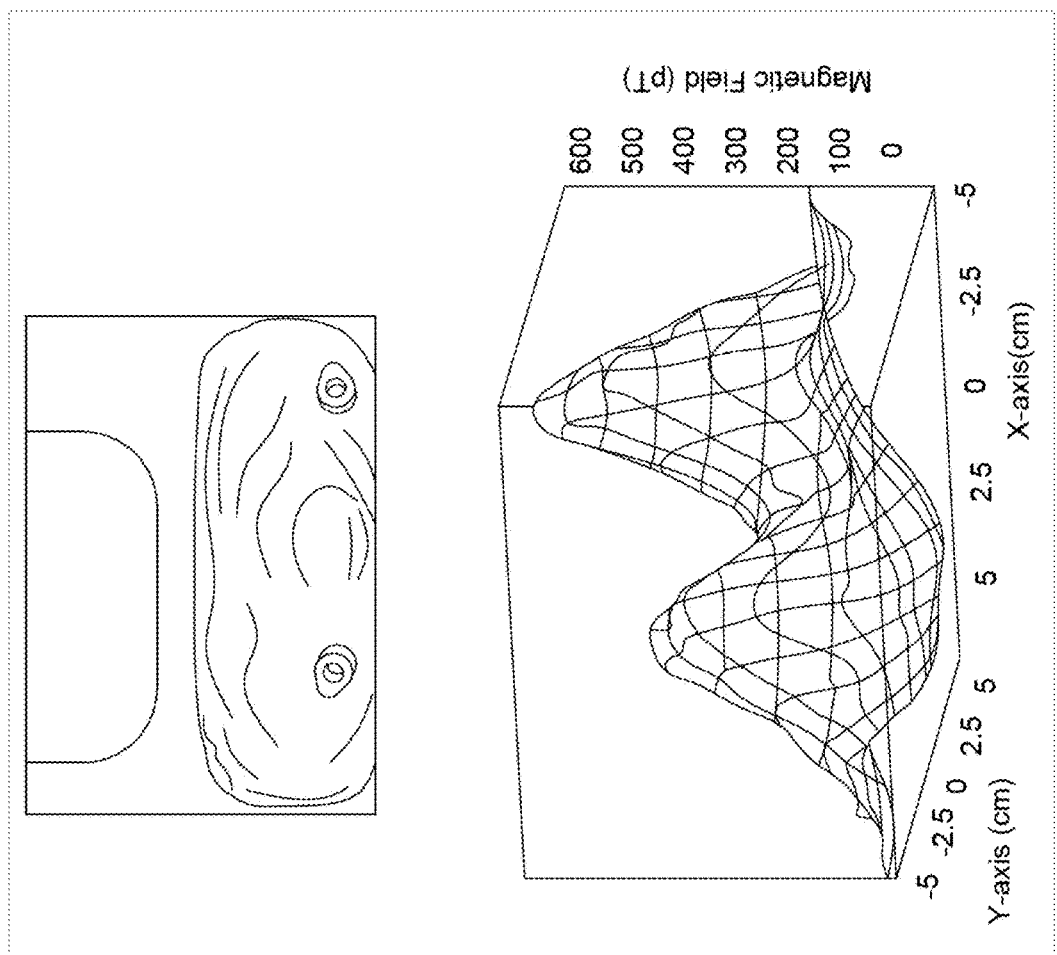
FIG. 12 is an illustration of a phantom with inserted vials of MCF7 Cells, left 2E+06, right=1E+06 cells.

A breast phantom was constructed using a standard mammogram calibration phantom as a model. The phantom was constructed out of clay; non-metallic material is transparent to these fields. Vials containing live cells were inserted into the phantom. FIG. 12 is an illustration of a phantom with inserted vials of MCF7 Cells, left=2E+06, right=1E+06 cells. Cells conjugated to HER2 Ab Using np from Ocean Nanotech. Fields mapped at five 7-channel SQUID positions=35 sites. 3-D contour maps represent the field distributions. Locations and moment magnitudes obtained from inverse problem. Moments determine the number of cells in vials from cell data shown above.

Figure 14:
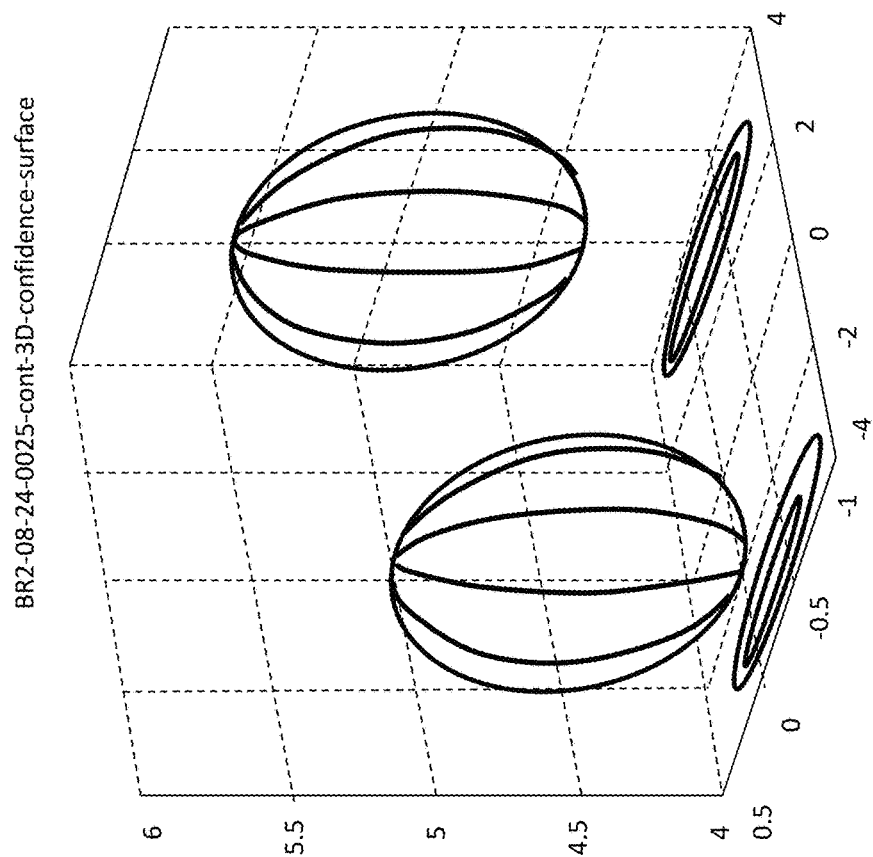
FIG. 14 contains position confidence plots obtained from mouse tumors.
Figure 13:
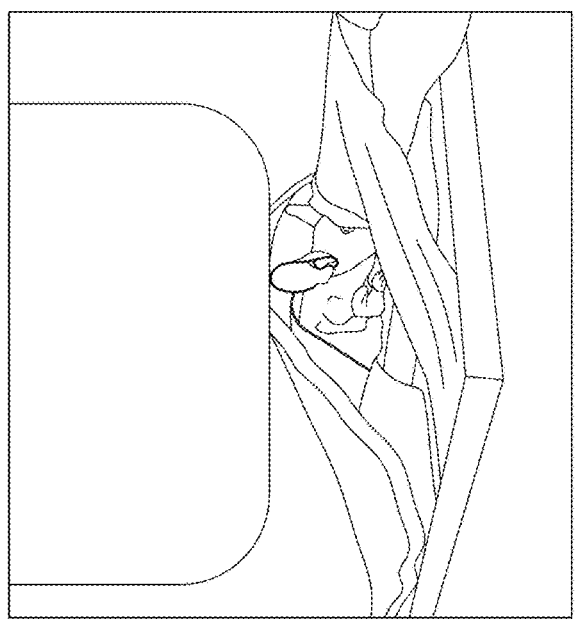
FIG. 13 is a photo of a nude mouse under a SQUID system.

A mouse model of breast cancer was developed appropriate for SQUID sensor measurements. SCID nude mice were used with human breast cancer cell lines. FIG. 13 is a photo of a nude mouse under a SQUID system. To study in-vivo processes by the SQUID technique, a mouse was injected with human MCF7 cells two weeks previously in two places. These cells then produced human tumors on the flanks of the mouse; one such tumor is visible behind the right ear of the mouse. The mouse was anesthetized through the tube over its mouth. Labeled magnetic nanoparticles were injected into the mouse at this stage either by tail, inter-peritoneal, or inter-tumoral injections. Subsequent to injections, the mouse was placed under the sensor system as shown and a magnetizing pulse was applied and the resulting magnetic moments of the injected particles were measured. As in the case of the live cancer cells, no moments were observed unless the particles had attached to cells within the tumors. In some cases both tumors were MCF7 type cells and in other cases, two different cell lines were used to develop the tumors in the mice. The mouse resided on the stage shown in FIG. 5 and could be moved to several positions under the sensor system to obtain more spatial information. Measurements were made as a function of time to determine how fast the particles were taken up from the blood stream and how fast phagocytosis occurred with the particles ending up in the liver. The mouse was typically placed at five stage positions under the 7-channel SQUID system to obtain 35 spatial locations. The magnetic fields at all positions were then used in a special code to solve the electromagnetic inverse problem using the Levenberg-Marquardt theorem to determine the location of all sources of magnetic particles in the mouse. This information was then compared to the known geometry of the mouse from photographs to determine the accuracy and sensitivity for locating breast cancer tumors in living animals. FIG. 14 contains position confidence plots obtained from mouse tumors. Left sphere is from left tumor that is ~2x right tumor in magnetic moment (see below). Positions calculated by a two dipole least squares method to extract magnetic moments and positions. Moments determine number of labeled cells in tumors.

Figure 18:
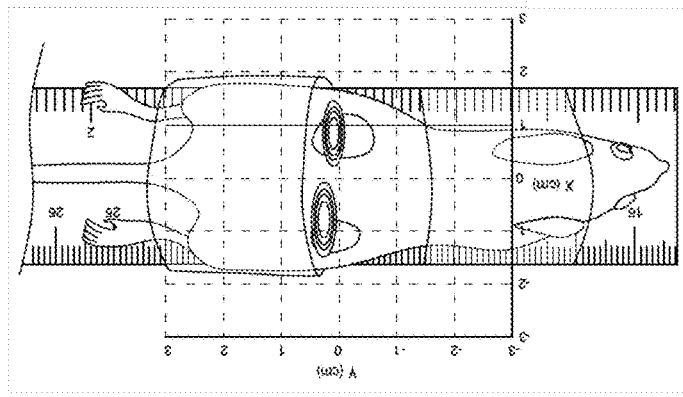
FIG. 18 is an illustration of the 2-dimensional 95% confidence limit for the locations of the two tumors superimposed on the actual tumors of the mouse.

The SQUID system results for in-vivo measurements on living animals are shown in FIGS. 16, 17, 18 for two different tumor bearing animals. Each mouse had two tumors but of different cell types. Different amounts of nanoparticles were absorbed by each of the two tumors. The mouse with MCF7 cells showed higher magnetic moments than the mouse with MDA-MB-231 tumors as expected due to the higher number of specific sites for HER2/neu antibodies on the former. FIG. 15 is an illustration of the magnetic contour lines observed for 35 different measurement sites as described in FIG. 13. Analysis of these magnetic fields yielded the spatial positions of the tumors that agreed with the measured values of these positions; the SQUID results giving higher precision than the physical measurements of approximately 3 mm. FIG. 16 is an illustration of the time course of the measurements for the two mice and both tumors of each mouse. The uptake of the particles occurred rapidly with the signal near maximum obtained in the first hour. The nanoparticles remain in the tumors for at least 5 hours, the length of the experiments. Subsequent to these measurements, the mice were euthanized and the tumors and other organs removed and placed under the sensor system to determine how much of the nanoparticle injections were in the tumors. The plots in FIG. 17 are illustrations of the results of these measurements and show very good agreement with the in-vivo measurements on the live mouse. In the lower left figure, a magnetic moment was observed in the liver indicating that some phagocytosis had occurred and the particles were delivered to the liver for elimination. Subsequent histology of the tumors also showed significant attachment of the particles to cells in the tumor using Prussian blue staining to emphasize the iron in the magnetic nanoparticles.

Figure 19:
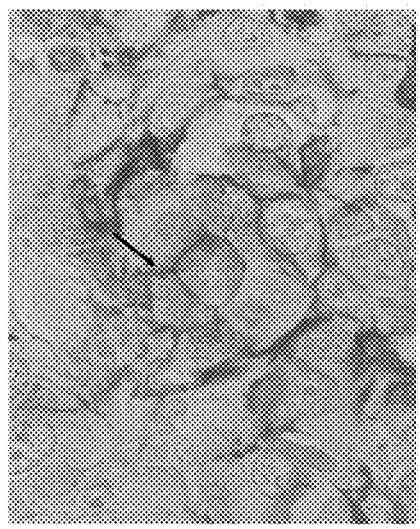
FIG. 19 is a photo of the histology of tumors after extraction.

Confidence regions were calculated for determining the accuracy of location of tumors for the in-vivo measurements of the mice. FIG. 18 is an illustration of the 2-dimensional 95% confidence limit for the locations of the two tumors superimposed on the actual tumors of the mouse. An accuracy of spatial location of approximately +/−3 mm is obtained in the x and y direction. FIG. 19 is a photo of the histology of tumors after extraction. Microscopic image of one MCF-7 tumor slice. Prussian Blue staining of cells reveals iron present in np attached to cells. Arrow points to cell covered with np.

A sensitive magnetic field sensor system has been demonstrated for in-vivo early detection of breast cancer by detecting magnetic nanoparticles, conjugated to antibodies for breast cancer cell lines. More than 1 million nanoparticles attach to each cancer cell. Method is sensitive to <100,000 cells at distances comparable to breast tumors. Standard x-ray mammography requires typically cell density of ten million cells. Measured moments are linear with cell number; i.e. measure of magnetic moment yields the number of cancer cells present. Very high contrast—nanoparticles not attached to cells are not observed. Phantom studies demonstrate multiple sources are localized accurately and number of cells per source determined. Mouse model was developed using multiple tumors of human breast cancer cell lines and in-vivo measurements made to determine the location and cancer cell count of these tumors subsequent to nanoparticle injections. Solutions of the inverse problem successfully locate tumors and number of cells. Histology confirms presence of np mouse tumors.

Example Application to Detection of Ovarian Cancer.

The etiology of ovarian cancer is not well understood and there is little evidence for risk factors suggesting preemptive screening. The normal screening test is pelvic examination if there are suspected symptoms, such as abdominal enlargement, and the results typically reveal advance stage of cancer. Routine screening of women presently is not done as there are no reliable screening tests. The great difficulty now with ovarian cancer is that by the time it is detected, it has metastasized from the ovary into other organs. For this reason, a hysterectomy is often performed along with the ovary removal. If the presence of ovarian cancer can be identified early and is contained in the ovary, the five year survival rate is 95%. However, only 29% are detected at this stage. If the disease has spread locally, this survival rate drops to 72% and if metastasized to distant locations, the rate of survival is 31%. Thus, development of early detection methods is imperative.

Figure 20:
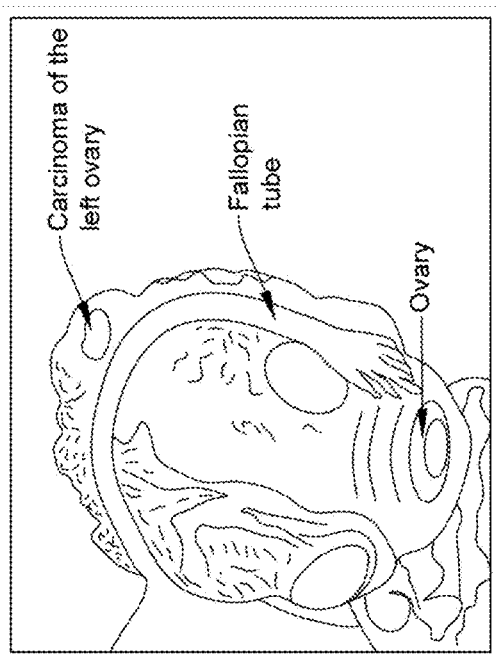
FIG. 20 is an illustration of an ovarian cancer showing the growth of the tumor on the ovary.
Figure 21:
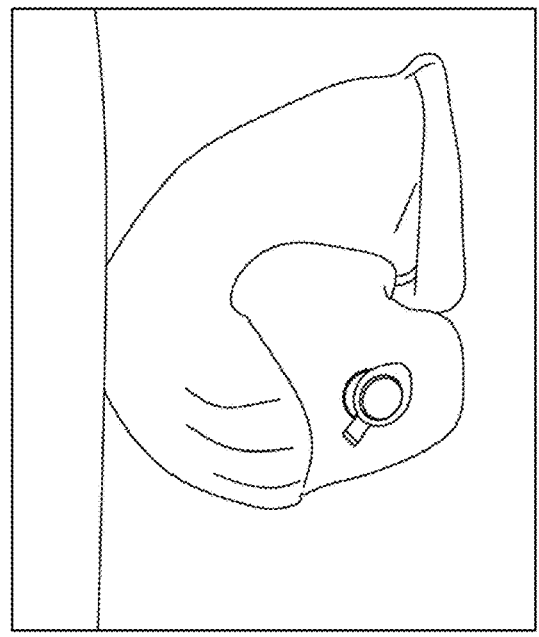
FIG. 21 is photograph of a full-size ovarian phantom placed under a SQUID sensor apparatus at a distance that would be typical of a patient subject.

FIG. 20 is an illustration of an ovarian cancer showing the growth of the tumor on the ovary. These tumors consist of cells with high numbers of receptors for the antibody CA-125 and can be targeted with magnetic nanoparticles labeled with this antibody. FIG. 21 is photograph of a full-size ovarian phantom placed under a SQUID sensor apparatus at a distance that would be typical of a patient subject. The phantom has a vial containing live ovarian cancer cells inserted into it. Magnetic nanoparticles labeled with the antibody CA-125 were inserted into this vial and because these antibodies are highly specific for these ovarian cancer cells, large numbers became attached to the cell surface. These magnetic nanoparticles were then detected by the SQUID sensor apparatus to provide sensitivity calibrations for in-vivo measurements for both animal and human in-vivo models.

Figure 22:
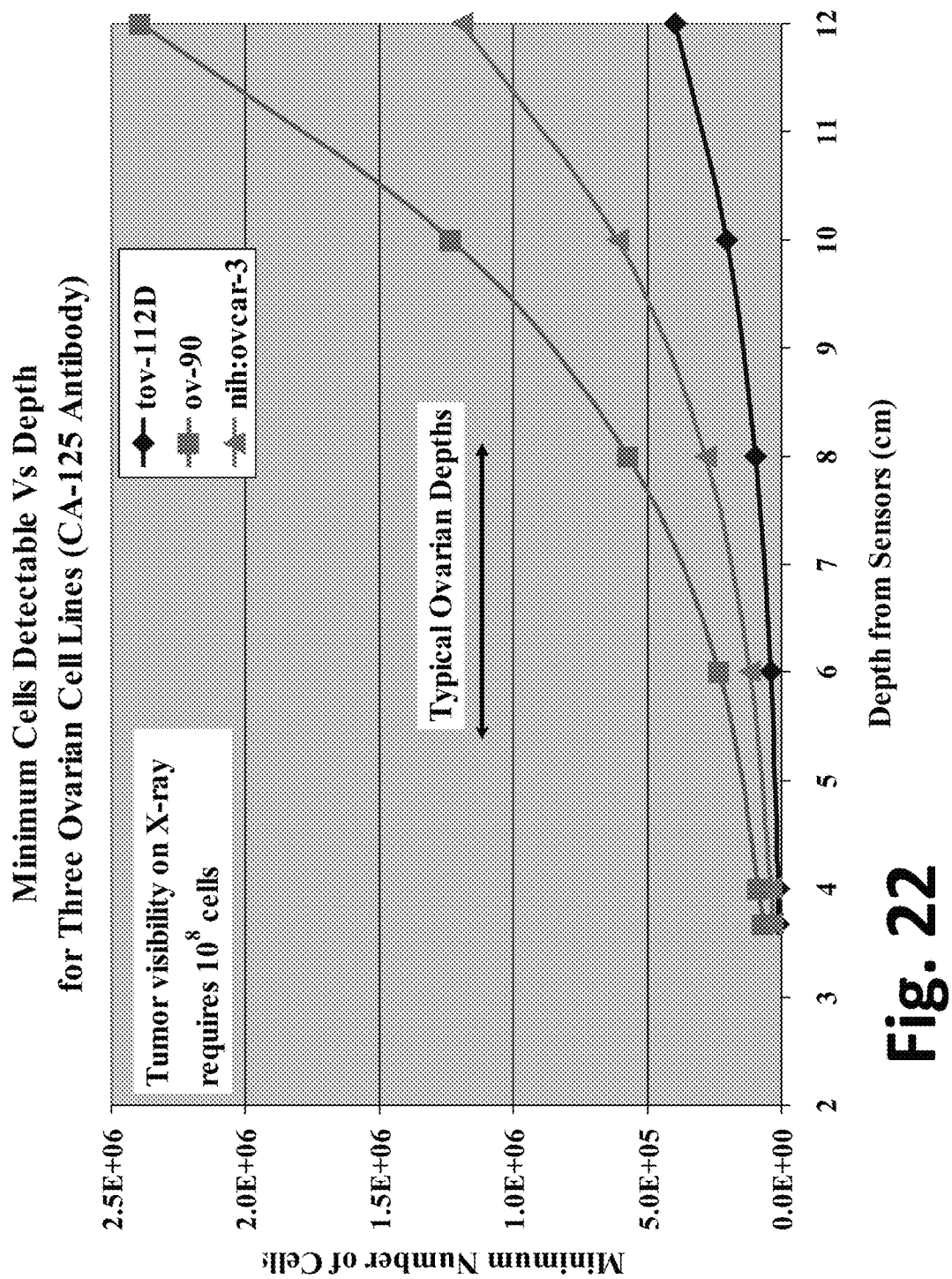
FIG. 22 is an illustration of the results of sensitivity studies for live ovarian cells inserted into the phantom shown in FIG. 21.

The results of the sensitivity studies for live ovarian cells inserted into the phantom shown in FIG. 21 are illustrated in FIG. 22 for three different ovarian cancer cell lines; namely, tov-112D, Ov-90, and nihovcar-3. The plot shows the minimum number of cells that were detected by this apparatus for the three different cell lines as a function of distance from the sensor to the patient's ovaries. The cancer cell line ov-90 is known to be one of the most aggressive of the cancers and these results indicate that there are many receptors for CA-125 on the surface of the cell.

Figure 23:
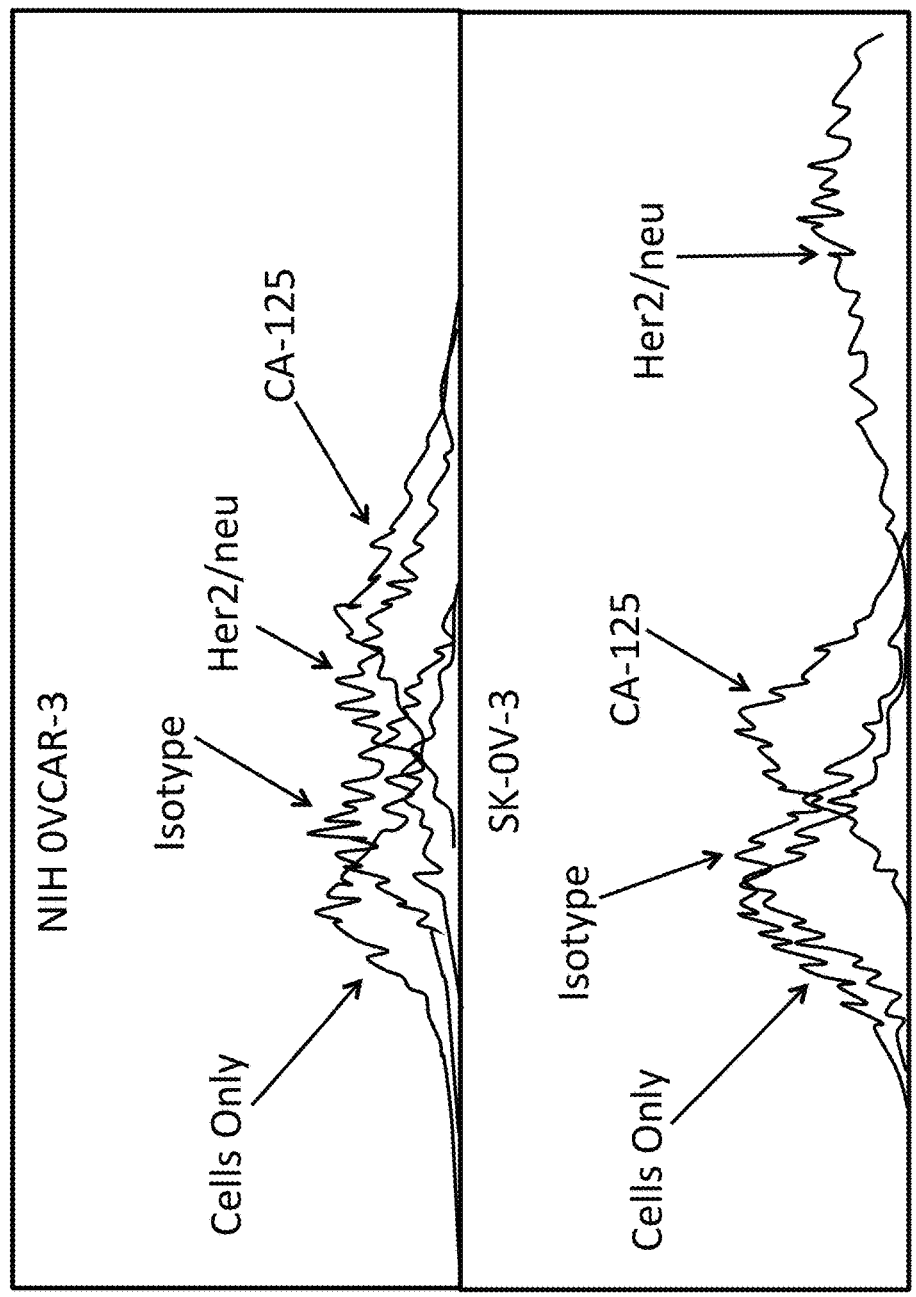
FIG. 23 is an illustration of confirmation of antibody sites for these cells using flow cytometry.

FIG. 23 is an illustration of confirmation of antibody sites for these cells using flow cytometry. FIG. 23 show two of the four cell lines examined. The signal from cells only is shown and the isotype (using a non-specific binding molecule, lgg), the Her2/neu antibody, and CA-125 antibody are shown with increasing site number to the right on these plots. These figures show that the CA-125 antibody has a large number of sites on these cells, with SK-OV-3 the largest of these two. The antibody Her2/neu is also specific to 30% of breast cancer cells.

Figure 24:
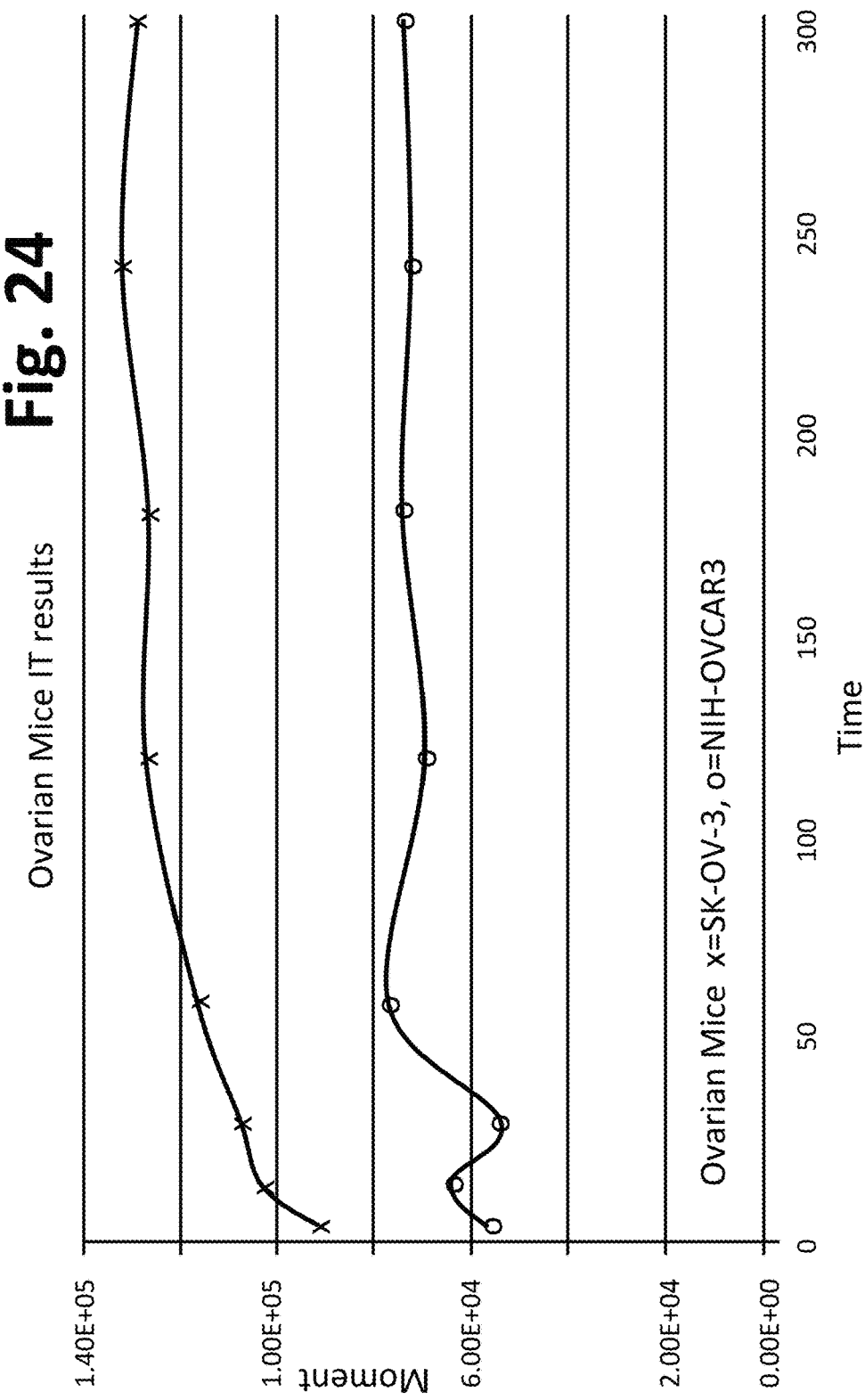
FIG. 24 is an illustration of magnetic moments from magnetic nanoparticles (from Ocean Nanotech) attached to ovarian human cancer tumors in the live mouse.

Measurements were made as a function of time to determine how fast the particles were taken up from the blood stream and how fast phagocytosis occurred with the particles ending up in the liver. Measurement of the magnetic moment in the SQUID sensor apparatus as a function of time for magnetic moments from magnetic nanoparticles (from Ocean Nanotech) attached to ovarian human cancer tumors in the live mouse is shown in FIG. 24. The mouse had two ovarian tumors, one of SK-OV-3 and the other of NIH-OVCAR3. The magnetic nanoparticles were coated with a carboxyl biocompatible coating and were then conjugated to the CA-125 antibody. This antibody is specific to ovarian cancer cells in humans. The labeled magnetic nanoparticles were injected into the mouse tumors and the magnetic moments of the mouse measured at various times ranging from one minute to 300 minutes. The uptake of the particles occurred rapidly with the signal near maximum obtained in the first hour. The time course indicates that the nanoparticles remain in the tumors for a number of hours. The nanoparticles remained in the tumors for at least 5 hours, the length of the experiments. Different amounts of nanoparticles were absorbed by each of the two tumors. The mouse tumor with SK-OV-3 cells showed higher magnetic moments than the mouse with NIH-OVCAR-3 tumors, as expected due to the higher number of specific sites for CA-125 antibodies on the former. The nanoparticles gave no magnetic moment before injection and only yield a magnetic signal when attached to something such as the cells in the tumor. Experiments have shown that injections into sites other than the tumor do not yield a signal as the particles do not bind to normal cells. After a period of time, the liver begins to show signs of accumulation of these particles as they are phagocytized from the system. Subsequent to these measurements, the mice were euthanized and the tumors and other organs removed and placed under the sensor apparatus to determine how much of the nanoparticle injections were in the tumors. These measurements agreed very well with the in-vivo measurements on the live mouse. Subsequent histology of the tumors showed significant attachment of the particles to cells in the tumor using Prussian blue staining to emphasize the iron in the magnetic nanoparticles.

A photograph of a mouse used to verify that the SQUID sensor method works in-vivo along with magnetic contour fields from this mouse are shown in FIG. 25. Human tumors are shown on the flanks of the mouse; these are the bumps above and to both sides of the tail in FIG. 25. These tumors were produced by injecting live human ovarian cancer cells into this severely-compromised-immune-deficient mouse and allowed to grow for several weeks until a 6-10 mm tumor was evident. The mouse was anesthetized through the tube over its mouth during all SQUID sensor experiments. Labeled magnetic nanoparticles were injected into the mouse at this stage either by tail, inter-peritoneal, or inter-tumoral injections. Subsequent to injections, the mouse was placed under a sensor as shown in FIG. 13 and a magnetizing pulse was applied and the resulting magnetic moments of the injected particles was measured. As in the case of the live cancer cells, no moments were observed unless the particles had attached to cells within the tumors. In some cases both tumors were SK-OV-3 type cells and in other cases, two different cell lines were used to develop the tumors in the mice.

The mouse placed on the stage shown in FIG. 5 could be moved to several positions under the sensor to obtain more spatial information. The mouse was typically placed at five stage positions under a 7-channel SQUID to obtain 35 spatial locations. The magnetic fields at all positions were then used in a code to solve the electromagnetic inverse problem using the Levenberg-Marquardt theorem to determine the location of all sources of magnetic particles in the mouse. This information was then compared to the known geometry of the mouse from photographs to determine the accuracy and sensitivity for locating cancer tumors in living animals. FIG. 25 shows the magnetic contour lines observed for 35 different measurements. Analysis of these magnetic fields yielded the spatial positions of the tumors that agreed with the measured values of these positions; the SQUID results giving higher precision than the physical measurements of approximately 3 mm.

Example Application to Detection of Hodgkin's Lymphoma.

Hodgkin's lymphoma (HL) accounts for 30% of all lymphomas. HL characteristically arises in lymph nodes, preferentially in the cervical regions, and thymus; but in advanced disease can involve distant lymph nodes, the spleen, and bone marrow. The majority of cases are in young adults between 15 and 34, but a second incidence peak occurs in people over 55. Currently, biopsy evaluation is required for diagnosis. Surgical biopsy has complications, such as infection and bleeding, and the evaluation of the biopsy typically takes 3-5 days. Thus, in HL cases in which the tumor mass is preventing blood return to the heart (i.e., superior vena cava syndrome, 10% of cases), significant morbidity or mortality can occur during this waiting period. Several of the antibodies that target Hodgkin's lymphoma; namely CD15, CD30, and CD25 have been identified. The latter antibody, however, targets many cells and is less specific. Another application where the present invention can have significant clinical impact is in the detection of persistent HL after therapy. If a patient experiencing a relapse undergoes high-dose radiation therapy, there is a good prognosis if the relapse is detected early. Patients who have a relapse will have a prognosis determined primarily by the duration of the first remission. The persistence of large fibrotic nodules, particularly in the mediastinum, after therapy leads to uncertainty in the determining whether persistent cancer is present and surgery of fibrotic nodules is fraught with difficulty to control bleeding problems and patient morbidity.

The relaxometry method of the present invention can provide a quantitative estimation of the number of lymphoma cells present in organs affected by Hodgkin's disease, such as the thymus and spleen. The RS cells are giant cells derived from B-lymphocytes that contain millions of receptors for CD30 and CD15. Previous results with SQUID sensors targeting T-cell lymphocytes have shown that for smaller cells, approximately a million nanoparticles can be attached to each T-cell. Steric hindrance limits the number of nanoparticles attached to a normal lymphocyte but the much larger RS cells can have 25 to 50 times more bound nanoparticles. The amount of iron per nanoparticle is $4.4 \times 10^{-6}$ ng/np. Given the large size of the RS cells, there can be several million nanoparticles per cell so that each cell may have up to 10 ng of iron. One hundred RS cells accumulated in the spleen or thymus can contain a microgram of iron. Less than a microgram is adequate for SQUID detection, therefore a detectability of 100 RS cells is possible. The measured amplitude of the residual magnetization of the antibody-labeled nanoparticles in vivo can provide an important diagnostic tool in lymphoma cancer. The signal strength depends on the density of antigens on the tumor cell surfaces and thus the field strength produced by the nanoparticles is proportional to the number density of antigenic sites on lymphoma cells. Particle number and density can be determined to provide the amplitude of the detected magnetic field. This information can be used in planning in vivo detection, as well as for assisting in the choice of nanoparticles to be used. The SQUID sensor is an ideal sensor system for Hodgkin's disease with large sensitivity for RS cells and in-vivo detection of the disease without biopsies and the ability to monitor the treatment of the disease during chemotherapy.

Figure 26:
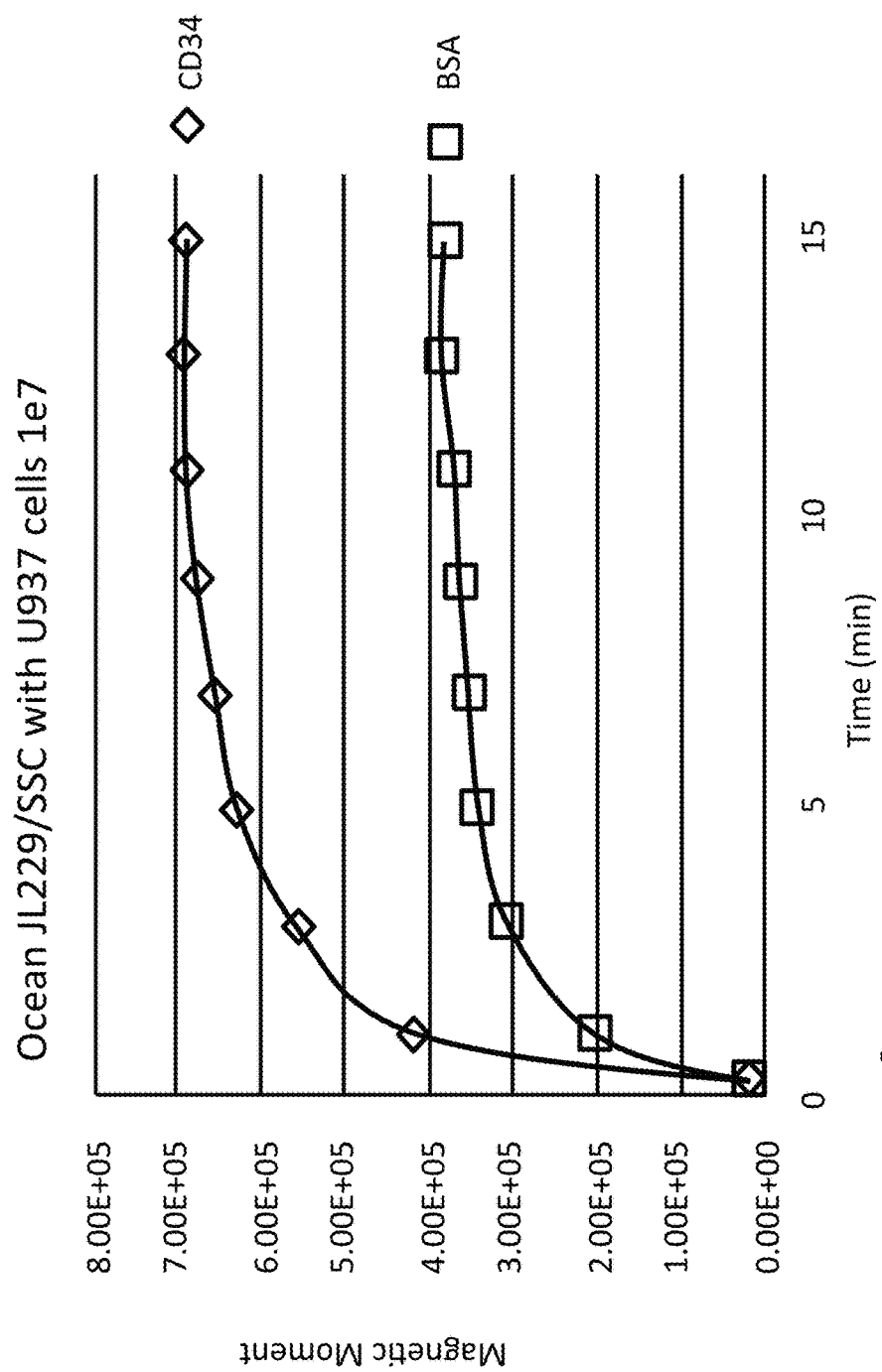
FIG. 26 is a graph of a measurement of the magnetic moment in a SQUID sensor system as a function of time for incubation of attaching magnetic nanoparticles to lymphoma cell lines.

FIG. 26 is a graph of a measurement of the magnetic moment in a SQUID sensor system as a function of time for incubation of attaching magnetic nanoparticles (from Ocean Nanotech) to lymphoma cell lines. The magnetic nanoparticles were coated with a carboxyl biocompatible coating and were then conjugated to the CD34 antibody. This antibody is specific to one type of lymphoma cells, namely, Acute Lymphomatic Leukemia in humans. The labeled magnetic nanoparticles were inserted into vials containing live cancer cells and the magnetic moments of the vial measured at various times ranging from one minute to 16 minutes. The zero time point is the magnetic moment of the vial of nanoparticles before adding to the cells. The lack of magnetic moment for the unmixed particles at time zero shows that unbound particles give no magnetic signal with this SQUID imaging method. Upon mixing with the cells, the magnetic moments increase rapidly and saturate indicating that the cells have collected on their surfaces with the maximum number of nanoparticles possible in one to two minutes. The top curve is for the lymphoma cancer cell line U937 that is known to be very specific for the CD34 antibody and the large magnitude of the magnetic signal verifies this. The lower curve is for the same cell line but a non-specific marker, BSA, and shows substantially smaller magnetic moments after incubation. The presence of a magnetic moment for the BSA is indicative of some phagocytosis of these cells where the nanoparticles enter the cells. U937 is a lymphoma of the T lymphocyte cells and RS is a lymphoma of the B lymphocyte cells. Since one of the principle purposes of lymphocyte cells is to take up particles that do not belong, this amount of non-specificity is expected. These results demonstrate the specificity of the antibody for the target cancer cells and verify that only bound particles give magnetic moments. This result is not true for other methods such as MRI which sees all particles, bound or unbound.

Samples of RS cells were obtained from the Tissue Bank facility at the University of New Mexico, a nationally recognized institution for cell banking and quantity of specimens. The efficiency of the SQUID sensor system for detecting RS cells was compared to the number of RS cells in a sample determined by manual hematocytometer counts. These isolated RS cells were labeled with nanoparticles specificity bound to CD15 and CD30 during the isolation procedure. Calibration of sensitivity was performed by serially dilution over a range of 1 in 10 to 1 in 100,000 cells. Ranges of nanoparticle density on malignant cells exceed $10^7$ nanoparticles/cell. The site density of CD15 is determined using a flow cytometry technique that quantifies receptors/cell. The number of CD15 and CD30 sites/cell was confirmed using a quantitative immunofluorescence staining technique.

Figure 27:
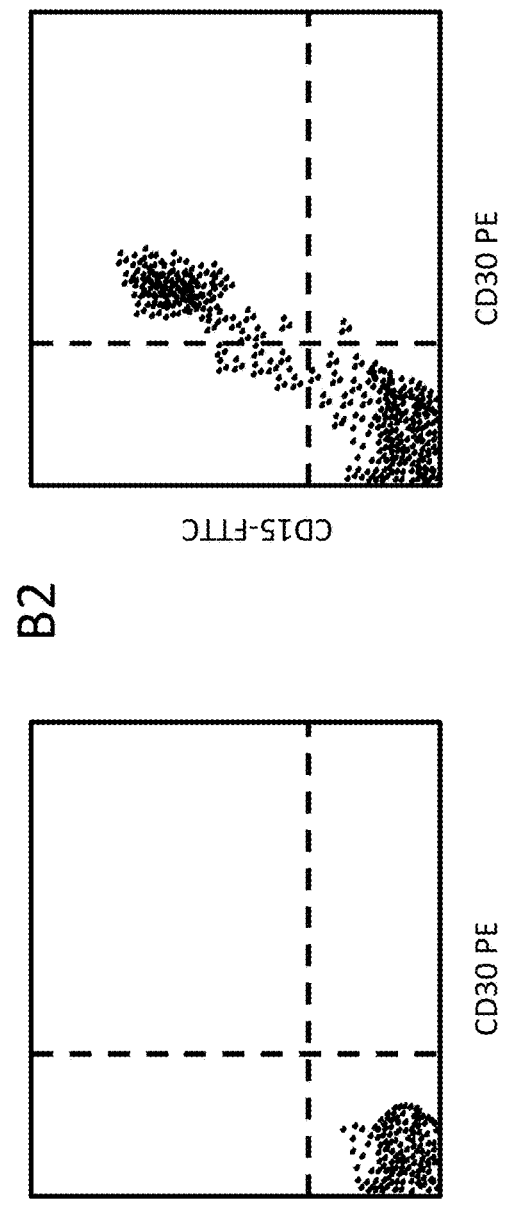
FIG. 27 is an illustration of the results of the flow cytometric measurements of RS cells from the lymphatic system in determining the number of sites available for nanoparticles and detection by the SQUID sensors.

FIG. 27 is an illustration of the results of the flow cytometric measurements of RS cells from the lymphatic system in determining the number of sites available for nanoparticles and detection by the SQUID sensors. FIG. 27A is a photograph showing the morphologic appearance of RS cells isolated from a lymph node specimen. FIG. 27B shows the flow cytometric analysis of a bone marrow sample where (B1) is before and (B2) after performing an enrichment procedure to enhance the frequency of RS cells in a sample for flow cytometry. Normally RS cells occur at a frequency of 1 in $10^4$ or $10^5$ of normal lymphocyte cells and must be enhanced before using CD15 and CD30 staining by flow cytometry in order to be detected. The SQUID sensor system detects all of the RS cells in-vivo and does not require sampling so enhancement is not necessary, as is required in the flow cytometry determinations.

Example Application to Detection of Prostate Cancer.

Prostate cancer has a high mortality rate due to the lack of early detection with standard screening technologies. The number of cases for 2009 in the US was 192,280 with 27,360 deaths. Prostate cancer accounts for 9% of male deaths and there is a 1 in 6 lifetime probability for developing prostate cancer. The disease is normally undetected until it has caused an enlargement of the prostate, urinary problems, or has spread to other organs. Asymptomatic detection of the disease is normally done by a digital examination, an elevated PSA test result, or a biopsy. The PSA test is now considered unreliable causing many unnecessary biopsies with accompanying dangers of infection. The digital examination is also highly subjective. Testing for prostate cancer is very controversial. The cost of PSA tests in the US alone exceed $3 billion and a recent study reported in the New England Journal of Medicine found that current screening methods do not reduce the death rate in men over 55 years old. The present invention can detect this cancer before it has metastasized.

An exemplary method to detect prostate cancer in a tissue comprises placing the patient on a measurement stage of a superconducting quantum interference device sensor apparatus; injecting a plurality of antibody-labeled magnetic nanoparticles into the patient for specific binding to the tissue in the patient; applying a uniform magnetizing pulse field to magnetize the nanoparticles injected into the patient; and detecting the residual magnetic field of the magnetized nanoparticles thereby providing an image of the nanoparticles bound to the tissue of the patient. The tissue can comprise prostate tissue and the antibody-labeled magnetic nanoparticles can specifically bind to antigens of prostate cancer cells. The antibody-labeled magnetic nanoparticle can comprise a magnetic core coated with a biocompatible coating to which is attached specific antibodies. For example, the magnetic core can comprise a ferromagnetic material, such as iron oxide. For example, the biocompatible coating can comprise Dextran, carboxyl, or amine. For the detection of prostate cancer, the specific antibody can be PSMA antibody.

The prostate-specific membrane antigen (PSMA) is a transmembrane glycoprotein that is highly expressed by most prostate cancers. It is also referred to as mAb 7E11. It is expressed on the surface of the tumor vascular endothelium of solid carcinomas but not on normal prostate cells. The amount of PSMA observed in prostate cancer follows the severity or grade of the tumor. Flow cytometry has shown that there are large numbers of receptor sites for this antibody on several cell lines of prostate cancer including LNCaP and PC-3, whereas a PSMA negative cell line, DU-145 indicates no expression. Results of attaching magnetic nanoparticles to these positive cell lines demonstrate one million or more nanoparticles per cell. These results are comparable to results from ovarian and breast cancer regarding nanoparticles per cell and depths of tumors in the body, and biomagnetic detection methods using SQUID sensors will have the same sensitivity for prostate cancer as ovarian cancer (described in one or more of the related applications incorporated by reference above). Results of studies on ovarian cancer can thus be directly applied to prostate cancer detection and localization. Compared to the CA-125 antibody for ovarian cancer, the PSMA is even more specific for in vivo prostate specific targeting strategies.

The SQUID sensor method can provide a quantitative estimation of microvascular structure in tumors leading to a new surrogate for vessel formation (angiogenesis) and individual tumor gradation. It has been shown in a study of tumor microvascular characterization in an experimental prostate cancer model using nanoparticles that tumor growth and aggressiveness/grade have a direct relationship to tumor neovascularization. Other studies estimate the concentration of magnetic particles in a tumor to be about 2.3 mg of nanoparticles per gram of tissue. This concentration is regularly achieved in the tumors of human liver cancer patients receiving treatment via intrahepatic arterially administered radioactive microspheres; the nanoparticles tend to concentrate in the vascular growth ring of a tumor. Less than a nanogram is adequate for SQUID detection. The measured amplitude of the residual magnetization of the antibody-labeled nanoparticles in vivo can provide an important diagnostic tool in prostate cancer. The signal strength depends on the density of antigens on the tumor cell surfaces and thus the field strength produced by the nanoparticles is proportional to the number density of antigenic sites on prostate tumor cells. Thus, particle number and density provides the amplitude of the detected magnetic field. This information can then be used in planning in vivo, as well as for assisting in the choice of nanoparticles to be used.

Example Application to Detection of Glioblastoma.

Brain cancer is particularly deadly and occurs in a number of forms. Cancer involving the glial cells is the most prevalent form and also the most aggressive brain tumor in humans. Various glial cells may be involved causing cancer of the type oligodendroglioma (involving the oligodendrocytes), astrocytoma (involving the astrocytes) and glioblastoma. The latter is the most frequently occurring of the brain cancers. These types of cancer normally results in death within a very short period of time. Gliablastoma cells can be targeted by markers such as EGFR, 8106, and PTN antibodies that may be used to image this type of cancer. Mouse models and brain cancer cell lines, such as U-251, are available for testing before human applications.

An important consideration in targeting brain cancer is the delivery across the blood brain barrier of the nanoparticles with markers attached. This barrier is somewhat opened in the vascular system associated with malignant tumors but still remains an impediment. The use of nanoparticles coated with lipophilic surfaces and then conjugated to antibodies or peptides increases the ability to cross the barrier. Additionally, the nanoparticle with markers can be encapsulated in a polymer coating with a liposome surface of in a micelle is another approach and releasing the conjugated nanoparticles from the polymer once inside of the brain using a slight application of a heating RF or ultrasound pulse.

An exemplary method to detect brain cancer comprises placing the patient on a measurement stage of a superconducting quantum interference device sensor apparatus; injecting a plurality of antibody-labeled magnetic nanoparticles into the patient for specific binding to the brain tumor in the patient; applying a uniform magnetizing pulse field to magnetize the nanoparticles injected into the patient; and detecting the residual magnetic field of the magnetized nanoparticles thereby providing an image of the nanoparticles bound to the tissue of the patient. The target is a brain tumor and the antibody-labeled magnetic nanoparticles can specifically bind to antigens of brain cancer cells. The antibody-labeled magnetic nanoparticle can comprise a magnetic core coated with a biocompatible coating to which is attached specific antibodies. For example, the magnetic core can comprise a ferromagnetic material, such as iron oxide. For example, the biocompatible coating can comprise Dextran, carboxyl, or amine. For the detection of glioblastomas, the specific antibody can be EGFR or similar antibody.

Angiogenesis EGFR has several forms and is a version of the epidermal growth factor receptor (EGFR) that is overexpressed by several types of cancer cells including glioblastoma cells and not normal cells. EGFR is currently undergoing immunotherapy clinical trials for patients with diagnosed glioblastoma. It can be conjugated with magnetic nanoparticles suitable for magnetic relaxometry detection and injected into the body. These magnetic nanoparticles can comprise a coating, such as polyethylene glycol (PEG), that will increase the efficacy of the targeted nanoparticles for penetrating the blood brain barrier. In another example embodiment of the present invention, the magnetic nanoparticles with markers attached can be contained within polymer coatings that are able to penetrate through the blood brain barrier and then released upon the application of a small RF heating pulse or the use of ultrasound. Results of attaching these angiogenesis peptides to magnetic nanoparticles and attaching these to cells are comparable to the use of other antibody results from ovarian and breast cancer regarding nanoparticles per cell and depths of tumors in the body. Biomagnetic detection methods using systems such as SQUID sensors will have the same sensitivity for brain cancer as ovarian cancer (described in one or more of the related applications incorporated by reference above). Results of studies on breast and ovarian cancer can thus be directly applied to brain cancer detection and localization.

Example Application to Detection of Pancreatic Cancer. A number of tumor markers are present in pancreatic cancer. CA19-9 is one example of a marker that is elevated in this cancer but is not very sensitive (77%) and non-specific (87%). Combinations of markers have been suggested by the M.D. Anderson Cancer Center and these are being tested for screening of pancreatic cancer. These markers are microRNAs and include miR-21, MiR-210, miR-155 and miR-196a. However, this combination also only achieves a low sensitivity (64%) but a higher specificity (89%) than the CA19-9. In addition, a number of antibodies have been identified against certain cell lines of human pancreatic cancer, for example the FG cell line and these include S3-15, S3-23, S3-41, S3-60, S3-110, and S3-53. Another identifying marker is the urokinase plasminogen activator receptor (uPAR) that is highly expressed in pancreatic cancer and also in tumor stromal cells. The latter marker has been used to deliver magnetic nanoparticles to pancreatic cancers grown as xenografts in nude mice. These markers have led to MRI detection of the tumors in the mice when used as labeled contrast agents. The mechanism is primarily delivery of the nanoparticles to the tumor endothelial cells.

There are no reliable imaging approaches for diagnosis of pancreatic cancer. Thus the development of biomarkers as a targeted imaging agent for MRI, or permitting the more sensitive technique of magnetic relaxometry, is a significant advance. MRI can detect small abnormalities in tumors and is also useful in determining if cancer has metastasized. Dynamic Contrast Enhanced (DCE) MRI potentially distinguishes between benign and cancerous tumors but produces a number of false positives. The expense of MRI limits its application as a screening tool. MRI imaging of tumors often uses magnetic nanoparticles as contrast agents as mentioned above and is an accepted protocol providing standards for the injection of such nanoparticles. Intravascular MRI contrast agents at a dose of 2 mg/kg of nanoparticle weight have been used to detect metastatic lesions. However, the use of MRI in pancreatic cancer is severely limited.

The present invention can provide a quantitative estimation of microvascular structure in tumors leading to a new surrogate for vessel formation (angiogenesis) and individual tumor gradation. It has been shown in results in a study of tumor microvascular characterization in an experimental pancreatic cancer model using nanoparticles that tumor growth and aggressiveness/grade have a direct relationship to tumor neovascularization. Other studies estimate the concentration of magnetic particles in a tumor of ~2.3 mg of nanoparticles per gram of tissue. This concentration is regularly achieved in the tumors of human liver cancer patients receiving treatment via intrahepatic arterially administered radioactive microspheres; the nanoparticles tend to concentrate in the vascular growth ring of a tumor. Nanograms are adequate for detection by the present invention. The measured amplitude of the residual magnetization of the antibody-labeled nanoparticles in vivo can provide an important diagnostic tool in pancreatic cancer. The signal strength depends on the density of antigens on the tumor cell surfaces and thus the field strength produced by the nanoparticles is proportional to the number density of antigenic sites on pancreatic tumor cells. Particle number and density can be determined to provide the amplitude of the detected magnetic field. This information can be used in planning in vivo detection, as well as for assisting in the choice of nanoparticles to be used. Examples of pancreatic cancer cell lines include FG or MIA PaCa-2 that are known to be specific for the uPAR antibody.

Combining Measurement with Therapy

In some embodiments of the present invention, the same particles can be used for hyperthermia therapy by application of external radio-frequency fields to oscillate and heat the particles and destroy the attached cells. In some embodiments, the same magnetic nanoparticles can be used to deliver anti-cancer drugs to the tumor where they are released exactly at the site of the cancer cells and not throughout the body.

Magnetic nanoparticles used in this invention can be specifically targeted to the cancer cells through antibodies or angiogenesis molecules and through multi-functional coatings of the particles can carry the drugs to the specified cells. Some embodiments of the present invention provide methods to enhance drug delivery at the tumor sites by the use of external magnetic fields to concentrate the magnetic nanoparticles. The biomagnetic sensors used to locate the cancer sites can then be used to monitor the treatment to determine when the cancer cells are destroyed and the dead cells that contain attached magnetic nanoparticles have been removed by phagocytosis. The high sensitivity of the biomagnetic sensor, as used in this invention, accurately assesses the effectiveness of the treatment and minimizes the use of therapy and unnecessary side effects.

The location of tumors is obtained using magnetic relaxometry methods with sensitive magnetic systems, such as biomagnetic Superconducting Quantum Interference Detectors (SQUIDs), and injected superparamagnetic nanoparticles labeled with antibodies specific for the type of cancer being detected. Superparamagnetic nanoparticles labeled with peptides targeting the microvascular structure supplying blood to the tumor can also be suitable for localizing the tumor. The nanoparticles connect to the cancer cells in the tumor, typically several hundred thousand nanoparticles per cell. The SQUIDs are sensitive to nanogram amounts of these nanoparticles and detect tumors thousands of times smaller than conventional x-ray sensors such as mammograms.

In some embodiments of the present invention, when the precise location of the tumor is obtained, treatment can be applied by using external RF coils located exactly over the determined location of the nanoparticles as determined by magnetic relaxometry where the magnetic relaxation fields are measured by SQUID or other sensitive sensors, to oscillate the magnetic nanoparticles through their interaction with the RF field resulting in the cells, to which the nanoparticles are attached through antibodies or peptides, being heated and killed. In some embodiments of the present invention, anti-cancer drugs are attached to the magnetic nanoparticles either prior to injection or after localization of the tumor and released at the site by application of external RF heating pulse, ultrasound pulse, biochemical interaction with cell surface or other means. In some embodiments of the present invention, external magnetic fields are used to concentrate the magnetic nanoparticles containing the drugs at the tumor site. In some embodiments of the present invention, the above methods are used in combination.

Magnetic relaxometry methods using the SQUID sensors can be employed to monitor the treatment of various different modes of therapy. Measurements of the magnetic moment of the tumor due to the magnetic nanoparticles bound to the cells can be made prior to application of therapy to determine the number of cancer cells in the tumor. During the therapy, similar measurements can be performed to determine the efficacy of the treatment and to monitor cell death. Upon successful treatment, the observed magnetic moment will be reduced to the sensitivity level of the sensor system indicating all detectable cancer cells have been destroyed. The observed trend of cell destruction as a function of time of applied therapy can be used to extend the treatment beyond the detection limit to extrapolate to zero cancer cells remaining.

Figure 28:
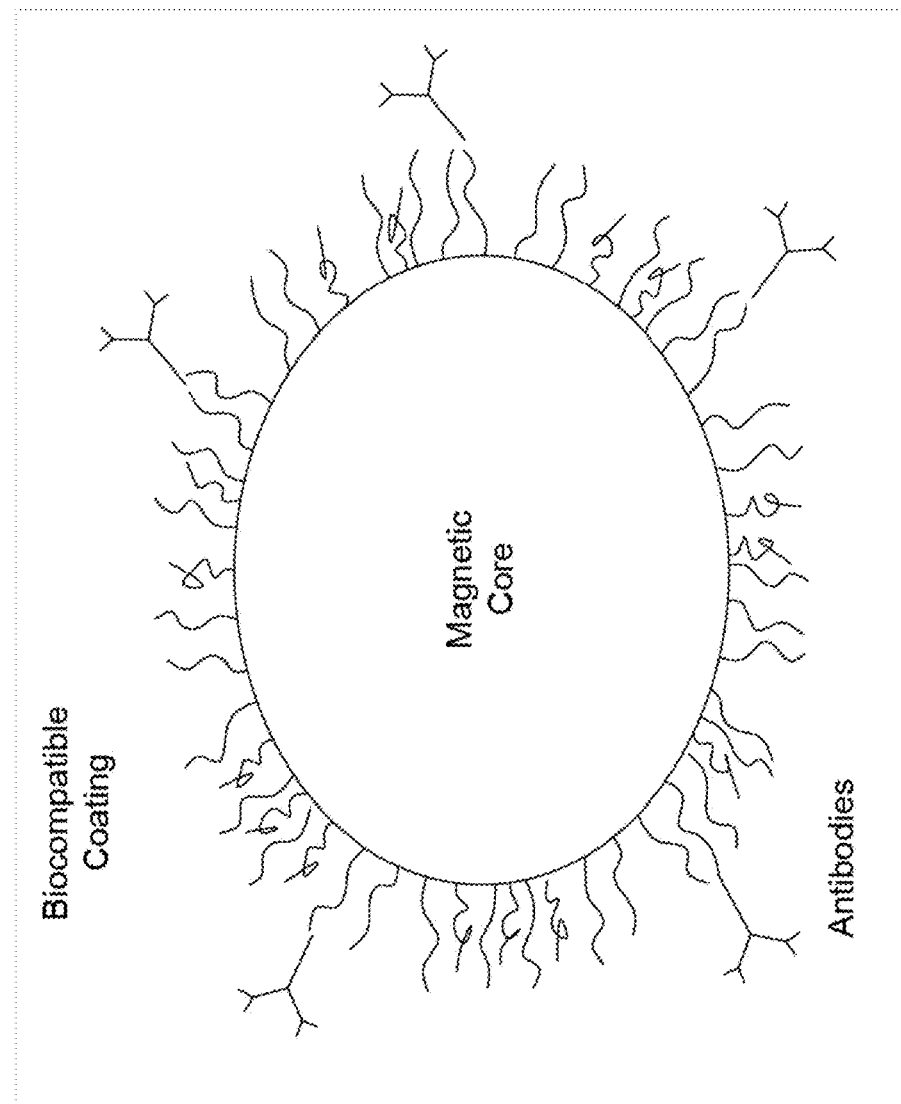
FIG. 28 is a schematic illustration of magnetic nanoparticles that can be used in the present invention for localization, hyperthermia and drug delivery in human cancer.

FIG. 28 is a schematic illustration of magnetic nanoparticles that can be used in the present invention for localization, hyperthermia and drug delivery in human cancer. A magnetic core comprises iron-oxide, for example magnetite or maghemite. The size of the core can be determined based on the characteristics of the magnetic system; for example a core of 24 nm in diameter can achieve desirable detection efficiency for Superconductive Quantum Interference Device (SQUID) sensors as described in the provisional applications referenced above. The superparamagnetic magnetic core is surrounded with a biocompatible surface permitting linking of various antibodies and peptides that are used for targeting the cells to be detected and for application of therapy using hyperthermia, drug delivery, or a combination of both. These antibodies link to this coating as illustrated in the figure.

Figure 29:
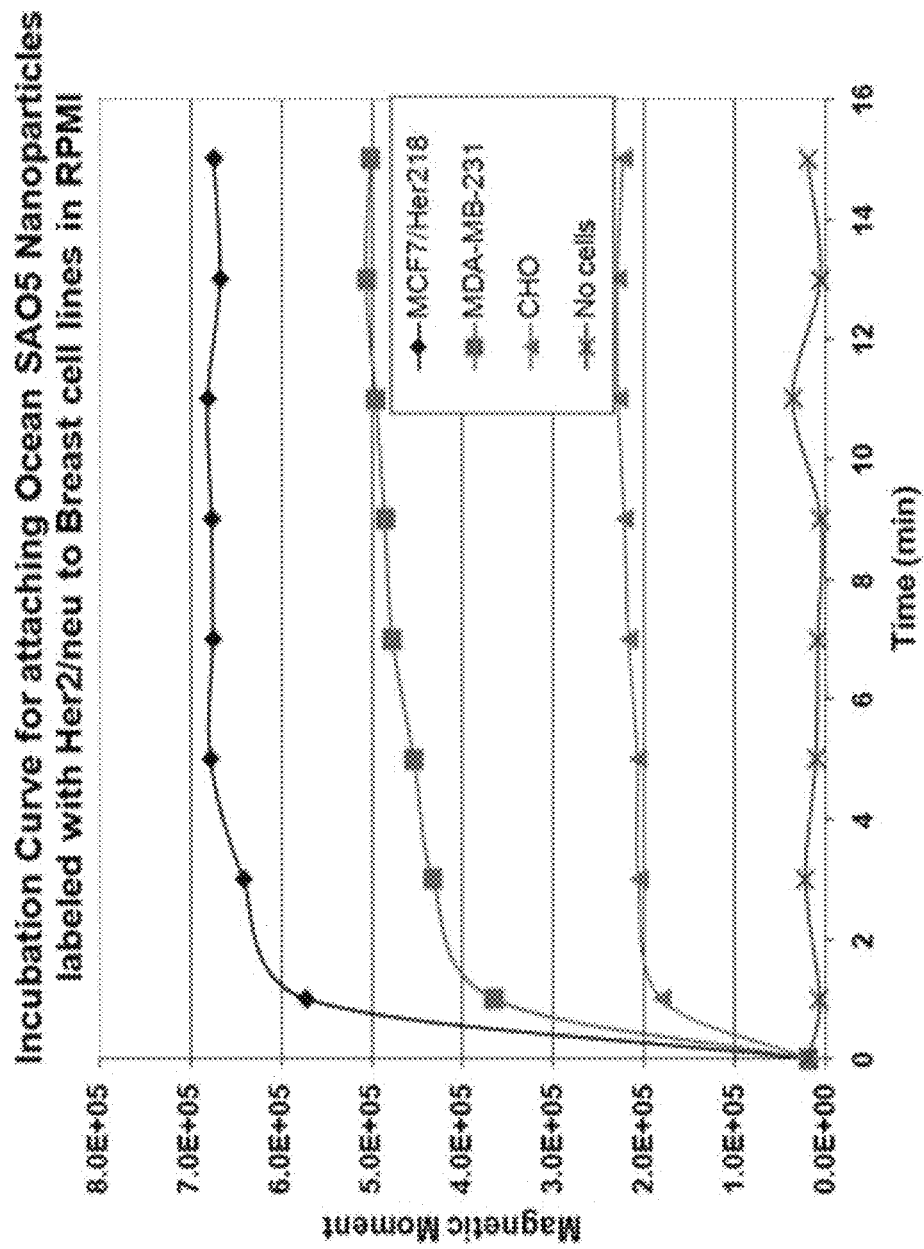
FIG. 29 is a graph of a measurement of the magnetic moment in a SQUID sensor system as a function of time for incubation of attaching magnetic nanoparticles to cancer cell lines in order to determine the number of nanoparticles per cell.

Determination of the number of nanoparticles per cell in order to determine the sensitivity for localization and the required strength of an applied field for hyperthermia can be performed by incubation measurements on cell cultures of the type of cancer under treatment. FIG. 29 is a graph of a measurement of the magnetic moment in a SQUID sensor system as a function of time for incubation of attaching magnetic nanoparticles to cancer cell lines in order to determine the number of nanoparticles per cell. FIG. 29 presents results for several breast cancer types, a non-breast cancer cell line, and for nanoparticles with no cells present. These results show that only particles attached to cell lines produce signals, and that the number of nanoparticles per cell can be used to determine the type of cancer cell present by measurement of the magnetic moment of known cells. This information can then be used to determine the sensitivity for detection and amount of hyperthermia to be applied.

For relaxometry detection and magnetic hyperthermia therapy, these nanoparticles can be injected into the blood stream or administered intratumorally. Delivery by ingestion can also be suitable in some applications. The particles are then exposed to an externally applied alternating magnetic field at the specific site identified by the SQUID sensors utilizing the relaxometry method to localize the tumor. This applied oscillating field generates heat specifically at the tumor region. The generated heat destroys cancer cells with minimal side-effects to the normal cells. The quantity of nanoparticles present in the tumor can be determined by the magnetic moment obtained from the relaxometry measurements giving the number of cancer cells present. The measurement of the number of nanoparticles connected to cells in the tumor is used to control the applied hyperthermia fields to produce sufficient heat production for cell destruction while preserving normal cells.

Figure 30:
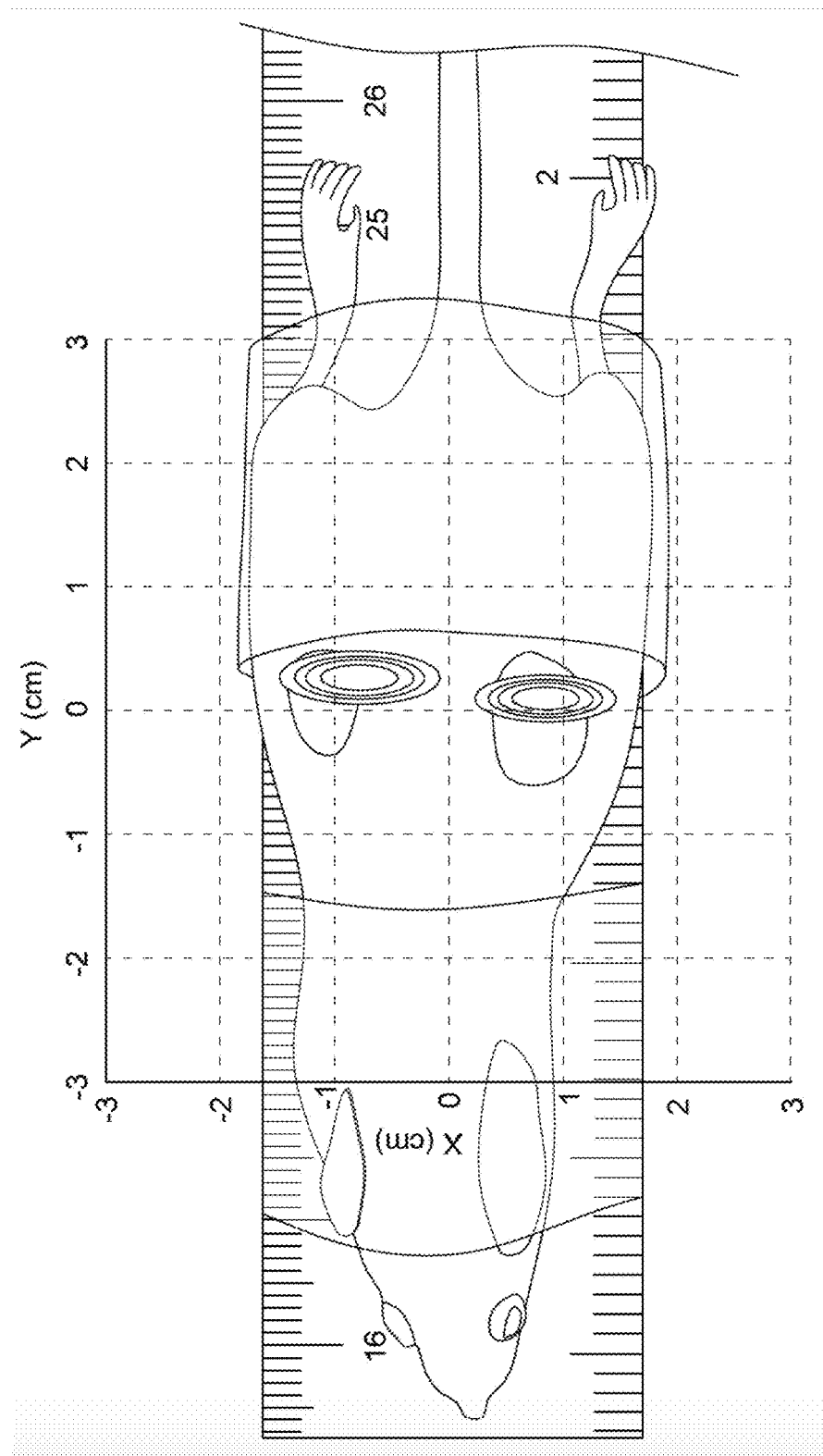
FIG. 30 is a photo of a mouse with tumors located by SQUID relaxometry.
Figure 31:
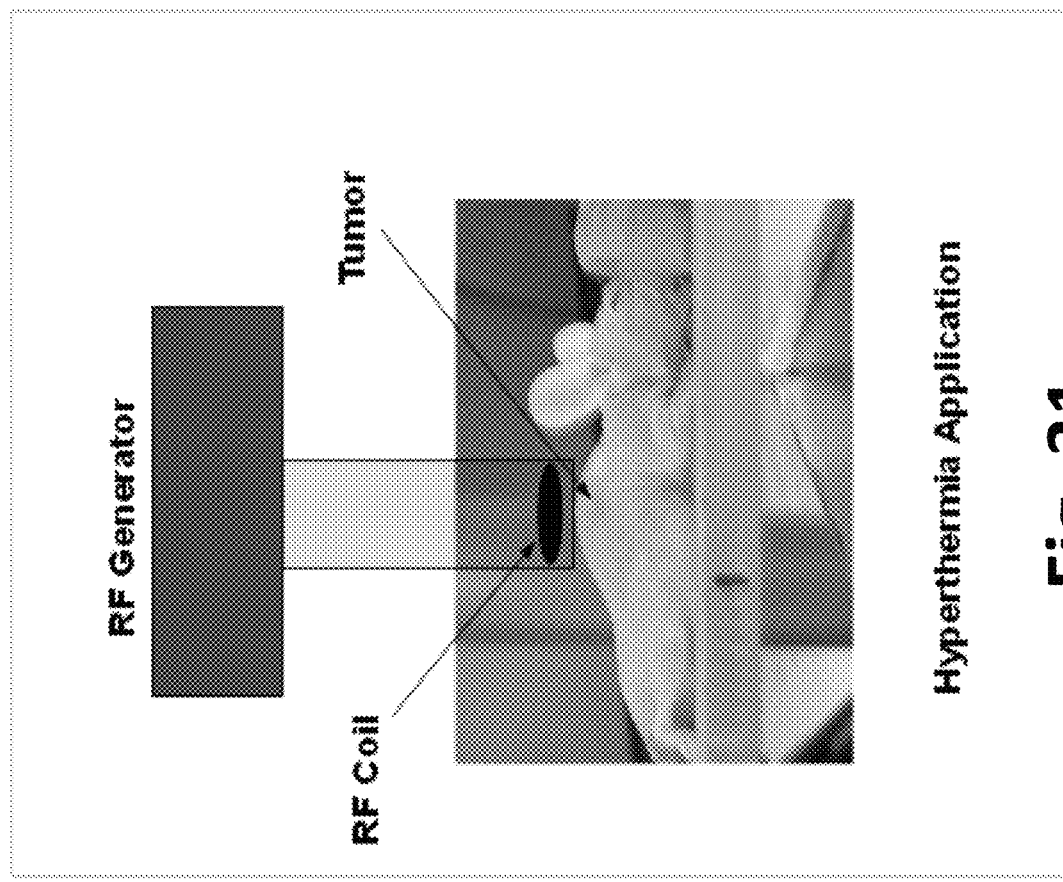
FIG. 31 is an illustration of applying hyperthermia to a tumor in an animal.

Small animal models are used to determine the capability of the SQUID relaxometry method for locating the tumors for subsequent hyperthermia therapy. FIG. 30 is a photograph of one such example. The locations of two tumors in this animal were obtained using relaxometry and superimposed on a Magnetic Resonance Image (MRI) of the animal. The ellipsoids in this figure show the confidence limits for localization as determined by magnetic relaxometry and guide the application of the magnetic field hyperthermia as illustrated in FIG. 31. The locations of the tumors by relaxometry are obtained by placement of the subject under a SQUID system and applying a short magnetization pulse to magnetize the nanoparticles that were injected to target the tumor cells. The distribution and magnitude of the resulting decaying magnetic fields is obtained by the SQUID system following the pulse. These results are compared to magnetic dipole sources through a Levenberg-Marquardt algorithm to yield the location of multiple tumors and the number of cancer cells present (through the location and total moment of the attached nanoparticles). In the example of FIG. 30 there are two tumors. This method is used to guide the hyperthermia treatment in both location and intensity and can be used as an in-vivo treatment of cancer. The localization of the application to the exact location of the tumor minimizes the side effects of the treatment, reduces the need for anesthesia, and reduces the recovery period as compared with application of hyperthermia fields over a large area of the body. Moreover, the magnetic relaxometry techniques can be used to monitor the effects of the treatment during the course of the hyperthermia application and can indicate when all of the cancer cells have been destroyed. Measurements at multiple times during treatment can be used to extrapolate the needed application of hyperthermia fields beyond the sensitivity of the SQUID system to detect the smallest tumor remaining, to determine complete destruction of the tumor.

Some embodiments of the present invention use (alone or in combination with other treatments such as hyperthermia as described above) magnetic drug targeting, where multifunctional nanoparticles are used to localize and to deliver anti-cancer drugs to a tumor. The localization can be done in a similar manner as described above in relation to hyperthermia treatment. FIG. 32 is an illustration of a multifunctional magnetic nanoparticle. The core of this particle can be the same as that illustrated in FIG. 28 with the addition of drugs designed to kill the cancer cells in the tumor. Once the multifunctional nanoparticle has attached to a cancer cell, the particle can be "opened" and the drug released to kill the cancer cell. FIG. 32 illustrates one method for delivering such drugs: a polymer coating binding the drugs to the particle can be opened using an external heat pulse. Other methods known to those skilled in the art can also be used to release the drug at the site.

Multifunctional nanoparticles can be administered by intra-arterial injection or by direct injection into the tumor at a site previously identified by magnetic relaxometry. In some embodiments, the multifunctional particles can be used to both identify the location of the tumor and also to deliver the drugs to the site. After location of the tumor by magnetic relaxometry, the particles can be concentrated at the site by external magnetic field forces, for example by using strong rare-earth magnets providing high gradient fields. This method can significantly increase the amount of anti-cancer drugs at the site while minimizing the amount of these drugs in other organs such as the liver and spleen and thereby reduce side-effects normally associated with conventional anti-cancer drug chemotherapy. It is possible to increase the concentration of drugs by several orders of magnitude using magnetic concentration over normal intra-arterial injection of the drugs with no concentration. The animal model shown in FIG. 31 exemplifies this method of therapy where the external magnetic fields are applied using strong, typically conical, magnets located directly over the sites identified by the confidence limits in this photograph. Histology of the tumors from this animal model has confirmed the large presence of nanoparticles in these tumors. Significant amounts of drugs delivered are estimated by the amount of iron delivered to these tumors as determined both by the SQUID relaxometry and by histology using Prussian blue staining of the iron in the tumor slices, with several hundreds of nanograms of iron measured indicating large amounts of drugs delivered. One example method of releasing anti-cancer drugs from multifunctional particles when targeted to cells by specific antibodies or peptides is through a small amount of heat application that is done using the hyperthermia alternating magnetic field applicator. Other methods including ultrasound bursts are also effective ways to release the particles. Similar to the application of hyperthermia, the effects of this treatment can be monitored by SQUID relaxometry and the end point of treatment determined.

Numerous studies have shown that the combined use of hyperthermia and drug delivery can result in higher cancer cell death rate than the use of either individually. The use of multifunctional nanoparticles and SQUID relaxometry can be suitable for such combined use. Administration of nanoparticles to the subject can be used for localization of the tumor in using image-guided therapy. These same nanoparticles can then be used for hyperthermia and/or drug delivery through magnetic concentration as well as release of the drugs at the site. Such application of the present invention permits maximum therapy delivered at the exact site of the cancer-cell-bearing tumor while minimizing side effects due to delivery of unwanted therapy to normal cell sites, and can simultaneously provide a method for monitoring the therapy until the tumor is eliminated.

In an example embodiment, the present invention provides a method for determining the location and number of cells in a tumor comprising: (1) introducing to the tumor a plurality of superparamagnetic magnetic nanoparticles conjugated with biocompatible features that preferentially bind with features common to cells in the tumor, (2) subjecting the region of the tumor to a magnetic field of sufficient strength and for sufficient time to magnetize the nanoparticles, (3) measuring a residual magnetic field in the region of the tumor during a time after the net magnetic moments of nanoparticles not bound to cells have decayed and before the net magnetic moments of nanoparticles bound to cells have decayed, (4) determining the number of cells in the tumor from the residual magnetic field, and (5) determining the location of the tumor by the location of the residual magnetic field.

In a further example embodiment, the present invention provides a method for treating cancer, comprising (a) determining the location and number of cells in a tumor according to the previous example embodiment, and (b) applying a therapy to the patient. A further example embodiment further comprises (c) determining a measure of the number of cells in the tumor after treatment, then repeating steps (b) and (c) until a desired number of cancel cells have been eliminated from the tumor. In a further example embodiment, wherein step (b) comprises (b1) providing delivery packages, wherein a delivery package comprises a magnetic nanoparticle, a drug that harms cancer cells, and an inhibitor that inhibits action of the drug; (b2) introducing a plurality of delivery packages into a patient; (b3) applying a magnetic field to encourage the delivery packages to the location of a tumor; (b4) treating the patient such that the inhibitor is overcome and drug acts on the cancer cells. In a further example embodiment, the inhibitor comprises a coating that encapsulates the drug, and wherein treating the patient so that the inhibitor is overcome comprises applying a magnetic field such that the delivery packages generate heat, motion, or a combination thereof sufficient to disrupt the inhibitory function of the coating. A further example embodiment further comprises (c) determining from the magnetic effect of nanoparticles in the tumor a measure of the number of cells in the tumor remaining after such treatment, (d) repeating steps (b) and (c) until the number of cells remaining in the tumor is below a threshold value. A further example embodiment further comprises (c) determining a measure of the number of cells in the tumor by the magnetic effect of nanoparticles introduced into the tumor, (d) repeating steps (b) and (c) until the number cells remaining in the tumor is below a threshold value, wherein the number of cells remaining in the tumor is determined from a plurality of measurements. A further example embodiment further comprises (c) determining a measure of the number of cells in the tumor by the magnetic effect of nanoparticles introduced into the tumor, (d) repeating steps (b) and (c), with the treatment applied in step (b) adjusted based on the effectiveness of the treatment as evidenced at least in part from the measure of the number of cells remaining in the tumor, until the number cells remaining in the tumor is below a threshold value. In a further example embodiment, adjusting the treatment comprises one or more of adjusting the composition of a chemotherapy treatment, adjusting the dosage of a chemotherapy agent, changing the mode of treatment, adjusting the time of therapy application.

The present invention has been described as set forth herein in relation to various example embodiments and design considerations. It will be understood that the above description is merely illustrative of the applications of the principles of the present invention, the scope of which is to be determined by the claims viewed in light of the specification. Other variants and modifications of the invention will be apparent to those of skill in the art.

What is claimed is:

1. A method for determining the location and number of cells characteristic of a disease comprising: (1) introducing to the cells in vivo a plurality of superparamagnetic magnetic nanoparticles conjugated with biocompatible features that cause the nanoparticles to interact with the cells such that particles that interact with the cells are inhibited from rotating as rapidly as nanoparticles that do not interact with the cells, (2) after step (1), subjecting the region of the cells of interest to a magnetic field imparting energy to the nanoparticles to magnetize the nanoparticles, (3) measuring a residual magnetic field in the region of the cells during a time after the net magnetic moments of nanoparticles that do not interact with the cells have decayed and before the net magnetic moments of nanoparticles that do interact with the cells cells have decayed, and performing at least one of (4) determining the number of cells characteristic of the disease from the residual magnetic field, and (5) determining the location of the cells characteristic of the disease by the location of the residual magnetic field.

2. A method as in claim 1, wherein step (3) measuring a residual magnetic field comprises attenuating or removing the applied magnetic field and measuring the decay of a residual magnetic field after the applied magnetic field has been attenuated or removed.

3. A method for treating disease, comprising (a) determining the location and number of cells characteristic of the disease according to claim 1, and (b) applying a therapy to the patient.

4. A method as in claim 3, wherein step (b) comprises applying hyperthermia to the region of the cells.

5. A method as in claim 4, wherein applying hyperthermia comprises applying an oscillating magnetic field to the region of the cells, wherein the oscillating magnetic field generates heat by its effect on the nanoparticle/feature conjugates.

6. A method according to claim 3, further comprising (c) determining a measure of the number of cells characteristic of the disease after treatment, then repeating steps (b) and (c) until a desired number of cells characteristic of the disease have been eliminated from the tumor.

7. A method as in claim 3, wherein step (b) comprises (b1) providing delivery packages, wherein a delivery package comprises a magnetic nanoparticle, a drug that harms cells characteristic of the disease, and an inhibitor that inhibits action of the drug; (b2) introducing a plurality of delivery packages into a patient; (b3) applying a magnetic field to encourage the delivery packages to the location of a tumor; (b4) treating the patient such that the inhibitor is overcome and drug acts on the cells characteristic of the disease.

8. A method as in claim 7, wherein the inhibitor comprises a coating that encapsulates the drug, and wherein treating the patient so that the inhibitor is overcome comprises applying a magnetic field such that the delivery packages generate heat, motion, or a combination thereof at a level such that the inhibitor coating no longer prevents the drug from acting on the cells characteristic of the disease.

9. A method as in claim 3, further comprising (c) determining from the magnetic effect of nanoparticles a measure of the number of cells characteristic of the disease remaining after such treatment, (d) repeating steps (b) and (c) until the number of cells characteristic of the disease remaining is below a threshold value.

10. A method as in claim 9, wherein the nanoparticles used in steps (a) and (c) are the same as used in step (b).

11. A method as in claim 3, further comprising (c) determining a measure of the number of cells characteristic of the disease by the magnetic effect of nanoparticles introduced into the cells, (d) repeating steps (b) and (c) until the number cells characteristic of the disease is below a threshold value, wherein the number of cells characteristic of the disease remaining is determined from a plurality of measurements.

12. A method as in claim 3, further comprising (c) determining a measure of the number of cells characteristic of the disease by the magnetic effect of nanoparticles introduced into the cells, (d) repeating steps (b) and (c), with the treatment applied in step (b) adjusted based on the effectiveness of the treatment as evidenced at least in part from the measure of the number of cells characteristic of the disease remaining, until the number cells characteristic of the disease remaining is below a threshold value.

13. A method as in claim 12, wherein adjusting the treatment comprises one or more of adjusting the composition of a chemotherapy treatment, adjusting the dosage of a chemotherapy agent, changing the mode of treatment, adjusting the time of therapy application.

14. A method as in claim 3, comprising determining the location of the cells characteristic of the disease by the location of the residual magnetic field.

* * * * *